(12) United States Patent
Brisben et al.

(10) Patent No.: US 10,362,948 B2
(45) Date of Patent: *Jul. 30, 2019

(54) MULTI-VECTOR SENSING IN CARDIAC DEVICES WITH DETECTION COMBINATIONS

(71) Applicant: CARDIAC PACEMAKERS, INC., St. Paul, MN (US)

(72) Inventors: Amy Jean Brisben, St. Paul, MN (US); Venugopal Allavatam, Maple Grove, MN (US); Deepa Mahajan, Roseville, MN (US); Krzysztof Z. Siejko, Maple Grove, MN (US); Kevin G. Wika, Blaine, MN (US); Keith L. Herrmann, Minneapolis, MN (US); Stephen J. Hahn, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 129 days.

This patent is subject to a terminal disclaimer.

(21) Appl. No.: 15/297,605

(22) Filed: Oct. 19, 2016

(65) Prior Publication Data

US 2017/0113050 A1    Apr. 27, 2017

Related U.S. Application Data

(60) Provisional application No. 62/245,757, filed on Oct. 23, 2015, provisional application No. 62/245,738, (Continued)

(51) Int. Cl.
*A61B 5/04* (2006.01)
*A61B 5/042* (2006.01)
(Continued)

(52) U.S. Cl.
CPC ........ *A61B 5/04011* (2013.01); *A61B 5/0402* (2013.01); *A61B 5/04012* (2013.01); (Continued)

(58) Field of Classification Search
CPC ... A61B 5/04011; A61B 5/0402; A61N 1/362; A61N 1/3621; A61N 1/3622
See application file for complete search history.

(56) References Cited

U.S. PATENT DOCUMENTS

| 5,313,953 A | 5/1994 | Yomtov et al. |
| 5,331,966 A | 7/1994 | Bennett et al. |

(Continued)

FOREIGN PATENT DOCUMENTS

| EP | 2912997 A1 | 9/2015 |
| WO | 2009026571 A2 | 2/2009 |

(Continued)

*Primary Examiner* — Allen Porter
(74) *Attorney, Agent, or Firm* — Seager, Tufte & Wickhem LLP

(57) ABSTRACT

Methods and devices for combining multiple signals from multiple sensing vectors for use in wearable or implantable cardiac devices. Signals from multiple vectors may be combined using weighting factors and/or by conversion to different coordinate systems than the original inputs, which may or may not be normalized to patient anatomy. Signals from multiple sensing vectors may be combined prior to or after several analytical steps or processes including before or after filtering, and before or after cardiac cycle detection. Cardiac cycle detection information may be combined across multiple sensing vectors before or after analysis of individual vectors for noise or overdetection. Cardiac cycle detection information may also be combined across multiple sensing vectors to identify noise and/or overdetection.

18 Claims, 22 Drawing Sheets

Related U.S. Application Data filed on Oct. 23, 2015, provisional application No. 62/245,762, filed on Oct. 23, 2015, provisional application No. 62/245,729, filed on Oct. 23, 2015.

(51) Int. Cl.

| | | |
|---|---|---|
| *A61B 5/00* | (2006.01) | |
| *A61N 1/39* | (2006.01) | |
| *A61B 5/0452* | (2006.01) | |
| *A61N 1/362* | (2006.01) | |
| *A61B 5/0402* | (2006.01) | |
| *A61N 1/04* | (2006.01) | |
| *A61N 1/05* | (2006.01) | |
| *A61N 1/365* | (2006.01) | |
| *A61N 1/37* | (2006.01) | |
| *A61B 5/0456* | (2006.01) | |
| *A61B 5/0468* | (2006.01) | |
| *A61B 5/024* | (2006.01) | |
| *A61B 5/0245* | (2006.01) | |
| *A61B 5/0472* | (2006.01) | |

(52) U.S. Cl.
CPC .......... *A61B 5/0422* (2013.01); *A61B 5/0452* (2013.01); *A61B 5/0456* (2013.01); *A61B 5/0468* (2013.01); *A61B 5/686* (2013.01); *A61B 5/72* (2013.01); *A61B 5/7203* (2013.01); *A61B 5/7221* (2013.01); *A61N 1/046* (2013.01); *A61N 1/05* (2013.01); *A61N 1/0563* (2013.01); *A61N 1/3622* (2013.01); *A61N 1/3625* (2013.01); *A61N 1/36514* (2013.01); *A61N 1/3704* (2013.01); *A61N 1/3925* (2013.01); *A61N 1/3956* (2013.01); *A61N 1/3987* (2013.01); *A61B 5/0245* (2013.01); *A61B 5/02416* (2013.01); *A61B 5/042* (2013.01); *A61B 5/04017* (2013.01); *A61B 5/04028* (2013.01); *A61B 5/0472* (2013.01); *A61B 5/04525* (2013.01); *A61B 5/6869* (2013.01)

(56) References Cited

U.S. PATENT DOCUMENTS

| | | | |
|---|---|---|---|
| 5,348,008 | A | 9/1994 | Bomn et al. |
| 5,562,709 | A * | 10/1996 | White .................. A61N 1/3621 600/518 |
| 5,704,365 | A | 1/1998 | Albrecht et al. |
| 5,709,215 | A | 1/1998 | Perttu et al. |
| 6,393,316 | B1 | 5/2002 | Gillberg et al. |
| 6,728,572 | B2 | 4/2004 | Hsu et al. |
| 7,248,921 | B2 | 4/2007 | Palreddy et al. |
| 7,330,757 | B2 | 2/2008 | Ostroff et al. |
| 7,376,458 | B2 | 5/2008 | Palreddy et al. |
| 7,392,085 | B2 | 6/2008 | Warren et al. |
| 7,496,409 | B2 | 2/2009 | Greenhut et al. |
| 7,623,909 | B2 | 11/2009 | Sanghera et al. |
| 7,783,340 | B2 | 8/2010 | Sanghera et al. |
| 8,160,686 | B2 | 4/2012 | Allavatam et al. |
| 8,160,687 | B2 | 4/2012 | Warren et al. |
| 8,185,198 | B2 | 5/2012 | Palreddy et al. |
| 8,200,341 | B2 | 6/2012 | Sanghera et al. |
| 8,457,737 | B2 | 6/2013 | Bardy et al. |
| 8,494,630 | B2 | 7/2013 | Palreddy et al. |
| 8,565,878 | B2 | 10/2013 | Allavatam et al. |
| 8,600,489 | B2 | 12/2013 | Warren et al. |
| 8,670,826 | B2 | 3/2014 | Warren et al. |
| 8,706,215 | B2 | 4/2014 | Kaib et al. |
| 8,712,523 | B2 | 4/2014 | Sanghera et al. |
| 8,831,711 | B2 | 9/2014 | Freer et al. |
| 8,983,586 | B2 | 3/2015 | Zhang |
| 9,119,596 | B2 | 9/2015 | Sanghera et al. |
| 9,352,165 | B2 | 5/2016 | Zhang |
| 9,924,885 | B2 | 3/2018 | Stadler et al. |
| 2006/0069322 | A1 | 3/2006 | Zhang et al. |
| 2006/0235322 | A1 | 10/2006 | Simske et al. |
| 2007/0239220 | A1 | 10/2007 | Greenhut et al. |
| 2008/0269813 | A1 | 10/2008 | Greenhut et al. |
| 2010/0256699 | A1 * | 10/2010 | Makdissi ........... A61B 5/04012 607/5 |
| 2012/0046563 | A1 | 2/2012 | Allavatam et al. |

FOREIGN PATENT DOCUMENTS

| | | |
|---|---|---|
| WO | 2009111766 A2 | 9/2009 |
| WO | 2012151498 A2 | 11/2012 |

* cited by examiner

MULTI-VECTOR SENSING IN CARDIAC DEVICES WITH DETECTION COMBINATIONS

CROSS REFERENCE TO RELATED APPLICATIONS

The present application claims the benefit of and priority to U.S. Provisional Patent Application Ser. No. 62/245,757, titled SIGNAL QUALITY MONITORING FOR MULTIPLE SENSE VECTORS IN CARDIAC DEVICES, U.S. Provisional Patent Application Ser. No. 62/245,738, titled MULTI-VECTOR SENSING IN CARDIAC DEVICES WITH SIGNAL COMBINATIONS, U.S. Provisional Patent Application Ser. No. 62/245,762, titled MULTI-VECTOR SENSING IN CARDIAC DEVICES WITH DETECTION COMBINATIONS, and U.S. Provisional Patent Application Ser. No. 62/245,729, titled MULTI-VECTOR SENSING IN CARDIAC DEVICES USING A HYBRID APPROACH, each filed on Oct. 23, 2015, the disclosures of which are incorporated herein by reference.

BACKGROUND

A number of cardiac rhythm management products are available for the use in diagnosis and treatment of various conditions. These may include, for example, subcutaneous, transvenous, or intracardiac therapy devices such as pacemakers, defibrillators and resynchronization devices. Implantable, external and/or wearable cardiac monitors are also available. External or wearable therapy products may include defibrillator vests and external pacemakers, as well as automatic external defibrillators.

In some cardiac rhythm management products, a plurality of sensing electrodes may be provided for use in obtaining cardiac electrical signals for analysis of the patient's cardiac status. Some such products have sufficient sensing electrodes to define more than one sensing vector, with each sensing vector defined by a combination of 2 or more electrodes. Some devices select a primary sensing vector as the "best" vector for use in observing cardiac conditions. It may be useful to instead use data from multiple vectors simultaneously. New and alternative approaches to the use of data from multiple sensing vectors are desirable.

OVERVIEW

The present inventors have recognized, among other things, that a problem to be solved is the need for new and alternative approaches to the use of multiple sensing vectors in cardiac devices. In some examples, data from multiple vectors are combined together to generate a combined data stream. In other examples, data from multiple sensing vectors, and/or a combined data stream, are processed in parallel through portions of a cardiac signal analysis, with results of such analysis later being combined together. The point where the multiple parallel processing items come together varies in different examples. In at least one example, data across the multiple parallel processes are combined repeatedly while the parallel processes proceed forward.

This overview is intended to provide a summary of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
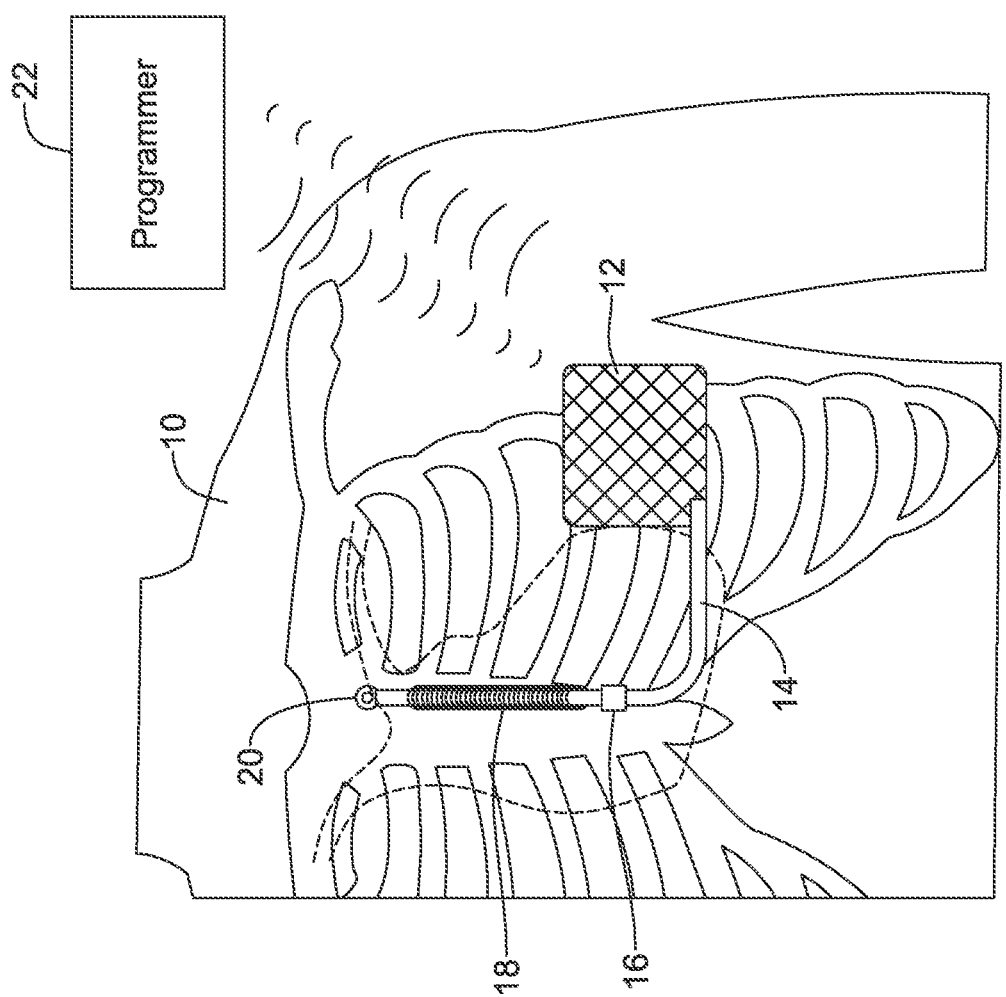
FIG. 1 shows an illustrative implantable medical device system with multiple sensing vectors available.

FIG. 1 shows the S-ICD System™ from Cameron Health, Inc., and Boston Scientific Corporation as implanted in a patient. The system is implanted in a patient 10 with a canister 12 in the left axilla at about the level of the cardiac apex. A lead 14 is placed subcutaneously, beneath the skin and over the ribcage of the patient, with a first portion extending along the inframammary crease to the xiphoid, and then superiorly parallel to and about 1-2 cm to the left of the sternum. A proximal sense electrode 16, shocking coil electrode 18, and distal tip sense electrode 20 are provided along the parasternal portion of the lead 14. The entire system is implanted outside of the ribcage.

The canister 12 may further include such components as would be appropriate for communication (such as RF communication, inductive telemetry or other suitable communication linkage) with an external device such as a programmer 22 or a bedside or home monitoring device. For example, during an implantation procedure, once the canister 12 and lead 14 are placed, the programmer 22 may be used to activate the canister 12 and/or direct/observe diagnostic or operational tests. After implantation, the programmer 22 may be used to non-invasively determine the status and history of the implanted device. The programmer 22 in combination with the canister 12 may also allow annunciation of statistics, errors, history and potential problems to the user/medical practitioner, and may also allow for updating of programming in the canister 12.

There several individual and combinational sensing vectors available with this implantation. In the commercial implementation there are three available sensing vectors: between electrode 16 and electrode 20, between electrode 16 and the metal housing of the canister 12, and between electrode 20 and the metal housing of the canister 12. If desired, the system could also be modified to use electrode 18 as a sensing electrode, paired with any of electrodes 16 and 20 or the metal housing of the canister 12. Moreover, it would be possible to combine two electrodes as a single pole for sensing, if desired.

The illustration in FIG. 1 is just one example. In additional examples, an implantable or wearable cardiac monitor may have multiple electrodes on a housing and/or lead to define two or more sensing vectors. Leadless devices, such as leadless cardiac pacemakers for implantation inside the heart, may have multiple sensing electrodes on or extending from a canister or housing to define multiple sensing vectors. Wearable defibrillators or pacemakers may also provide multiple cutaneous electrodes on the anterior and/or posterior thorax of the patient, and may even include indifferent electrodes elsewhere such as on a limb. Additional sensing data may be mathematically derived from combinations of the physical vectors provided by the sensing electrodes. Transvenous and/or epicardial implantable devices may have an active housing adapted for use in sensing along with plural electrodes for sensing on one or more leads, as is well known in the art. For example, a transvenous device may have a right ventricular lead with atrial and ventricular sensing electrodes as well as an indifferent electrode on the canister.

For any of these systems, the availability of multiple sensing vectors poses several questions, including how to determine which of several sensing vectors is or is not performing well, and how to decide whether to switch from one sensing configuration to another. The first generation of the S-ICD System shown in FIG. 1 incorporated sensing vector selection methods in the clinical setting while in communication with a programmer. Some details of such methods are discussed in U.S. Pat. Nos. 7,392,085, 7,623,909, and 8,200,341, the disclosures of which are incorporated herein by reference. The device did not automatically switch sensing vectors in response to identified sensing signal quality metric changes.

Some additional background discussion of the use of multiple vectors and sensing therewith is shown in U.S. Pat. No. 5,313,953, as well as U.S. Pat. No. 5,331,966 which additionally shows a device with multiple housing electrodes for sensing. While these prior discussions identify the possibility of ambulatory vector quality monitoring and switching, and/or combining multiple sense vector signals together, there remains additional need for alternatives and new devices and methods to perform signal quality monitoring, sense vector switching, and/or to provide for combining multiple sense vectors together. U.S. Provisional Application 62/245,757, titled SIGNAL QUALITY MONITORING FOR MULTIPLE SENSE VECTORS IN CARDIAC DEVICES, the disclosure of which is incorporated herein by reference, discusses monitoring signal quality with various metrics as well.

Figure 2:
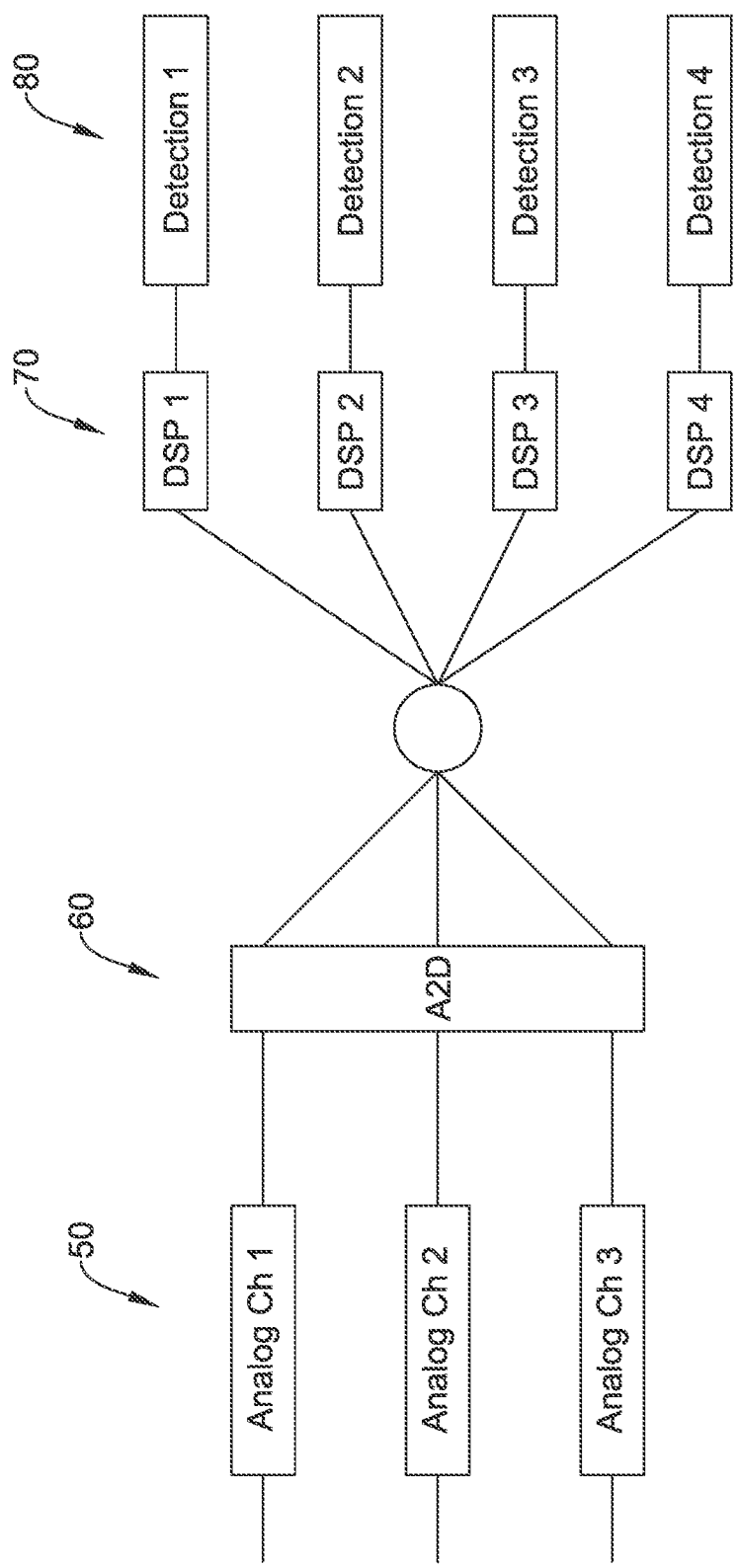
FIG. 2 shows schematically an illustrative input circuit design.

FIG. 2 shows an illustrative sensing input system. A plurality of analog input channels are defined as indicated at 50. The analog channels 50 may be dedicated or hard wired to a particular combination of sensing electrodes, or may be defined using a multiplexor or other switch array to couple to pairs or groups of sensing electrodes such as described above and/or in association with FIG. 1. The individual channels may include DC blocking, bandpass, notch, bandstop, 50/60 Hz blocking, and/or other filtering circuitry as well as amplification circuitry such as a low noise amplifier, either as stand-alone circuits or operating cooperatively with an analog to digital conversion (ADC) circuitry 60. Any suitable ADC circuitry may be used, including a wide array of such devices known in the art including delta-sigma, successive approximation, Wilkinson, ramp-compare, delta encoded, pipeline, integrating, etc.

In some examples only a subset of the analog channels 50 are converted at any given time; in other examples all of the analog channels 50 may be converted. The plurality of digital signals output by the ADC circuit can be assessed on one or plural digital signal processors (DSP) 70, or may be analyzed together in single processor. For power saving purposes, and to take advantage of modular design, it may be suitable to use dedicated DSP to yield a digital signal for use in detection circuits 80. Any suitable DSP circuit can be used at 70.

One element of DSP may be the inclusion of a digital filtering circuit to narrow the band of signals to a range generally between about 10 and 40 Hz, though wider or narrower ranges may be used. In addition, line signal filtering at 50 or 60 Hz, depending on geography, may be implemented in the DSP.

In some examples, a DSP has multiple stages. For example, a DSP may have five filter stages with each stage being a configurable bi-quad filter, or other filter. One or more stages may be used for 50 and 60 Hz notch filters to eliminate line noise. A bandpass can be generated with two other stages by having a low pass filter in the range of 15-40 Hz, or about 25 Hz in another example, and a high pass filter in the range of 1 to 15 Hz, with 9 Hz serving as one example. Where multiple signals are processed in parallel, not all signals will necessarily be filtered the same and, in some examples, one of the signals may filtered several different ways.

In some examples the individual detection blocks at 80 each use a separate cardiac cycle detection method to identify heart beats for use in one or more of defining a cardiac cycle signal for morphology (shape) analysis, and or to count cardiac cycles per unit time to generate a cardiac rate for a given chamber of the heart. Individual detection blocks at 80 may each use the same method of cardiac cycle analysis, or different methods may be selected for different digital signals. For example, if one detection line is configured for use on a signal captured using two intracardiac electrodes, and a different detection line uses a signal captured using two subcutaneous electrodes, the detection lines would likely each use a different mode of detection, as the intracardiac signal will look quite different from the subcutaneous signal. Some examples of cardiac cycle detection (also sometimes referred to as R-wave or beat detection) are shown in U.S. Pat. Nos. 8,565,878 and 5,709,215, the disclosures of which are incorporated herein by reference. Several methods are known in which a time varying threshold compared against the received cardiac signal until the threshold is crossed, at which point a beat or new cardiac cycle may be declared.

Figure 3:
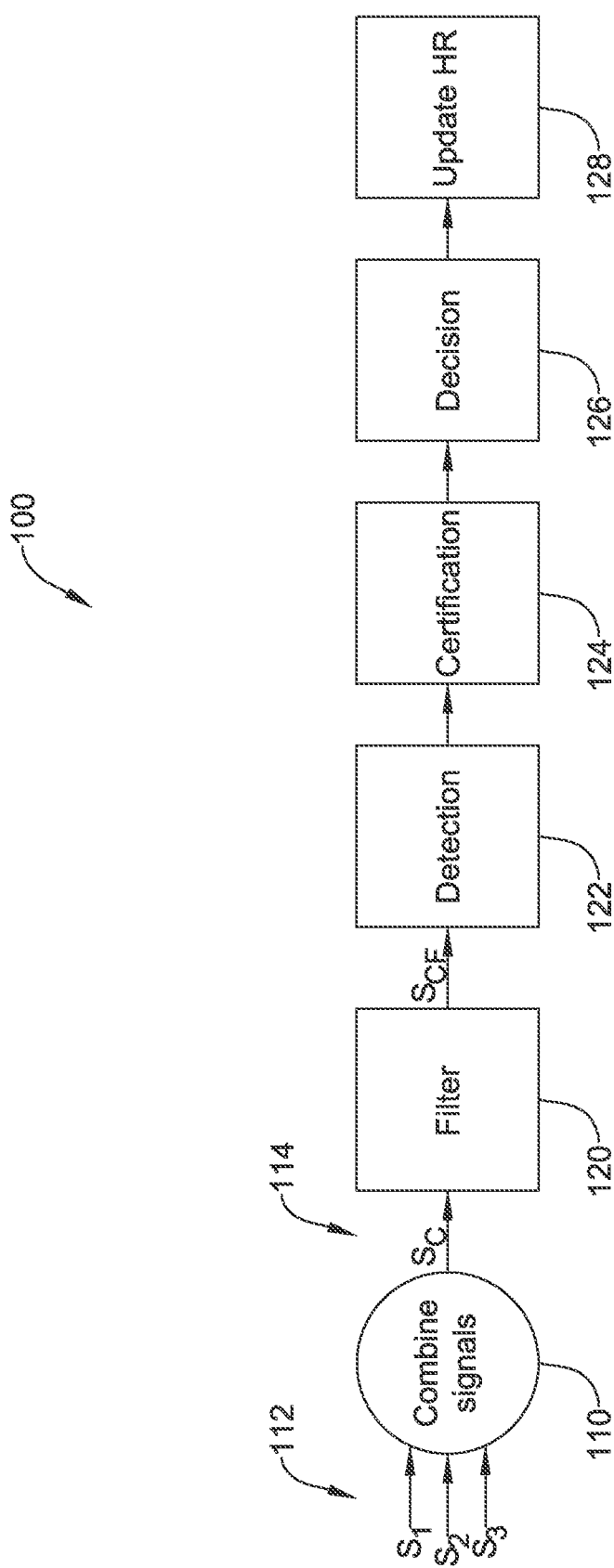
FIG. 3-11 show illustrative methods in block flow form.
Figure 4:
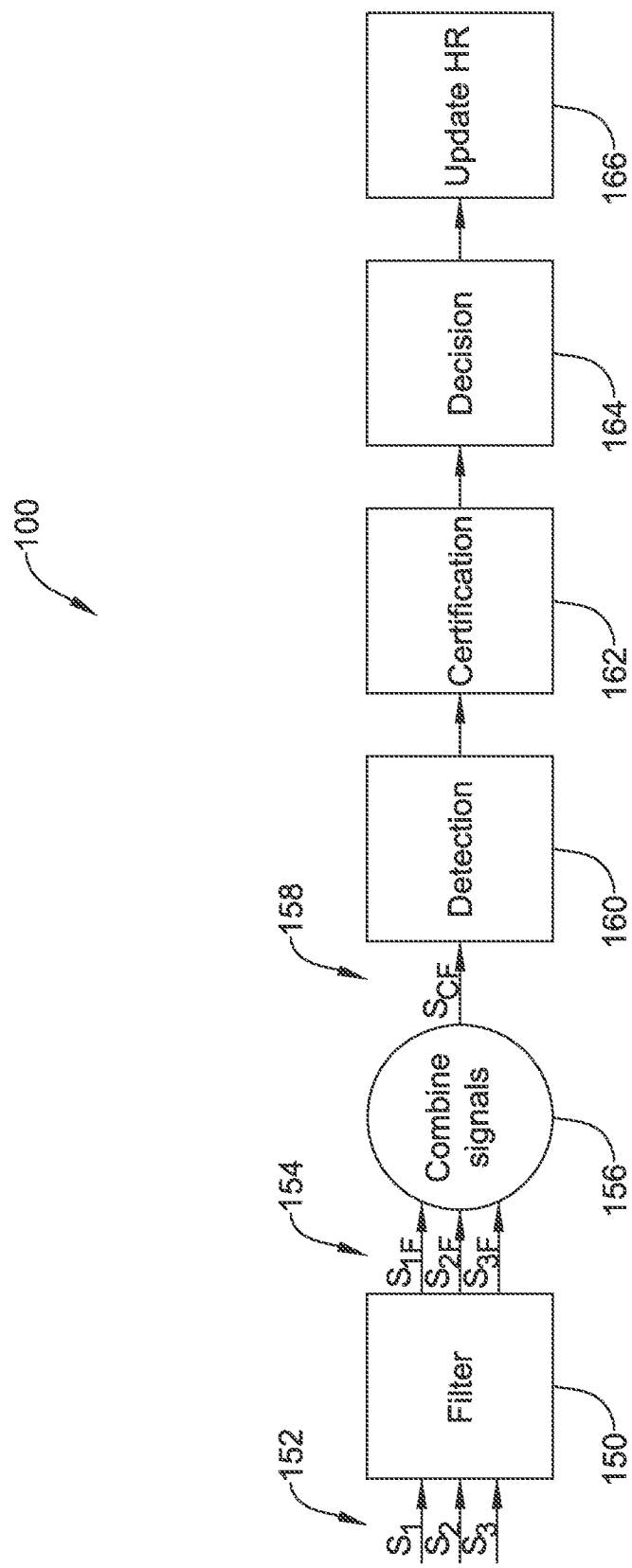
Figure 5:
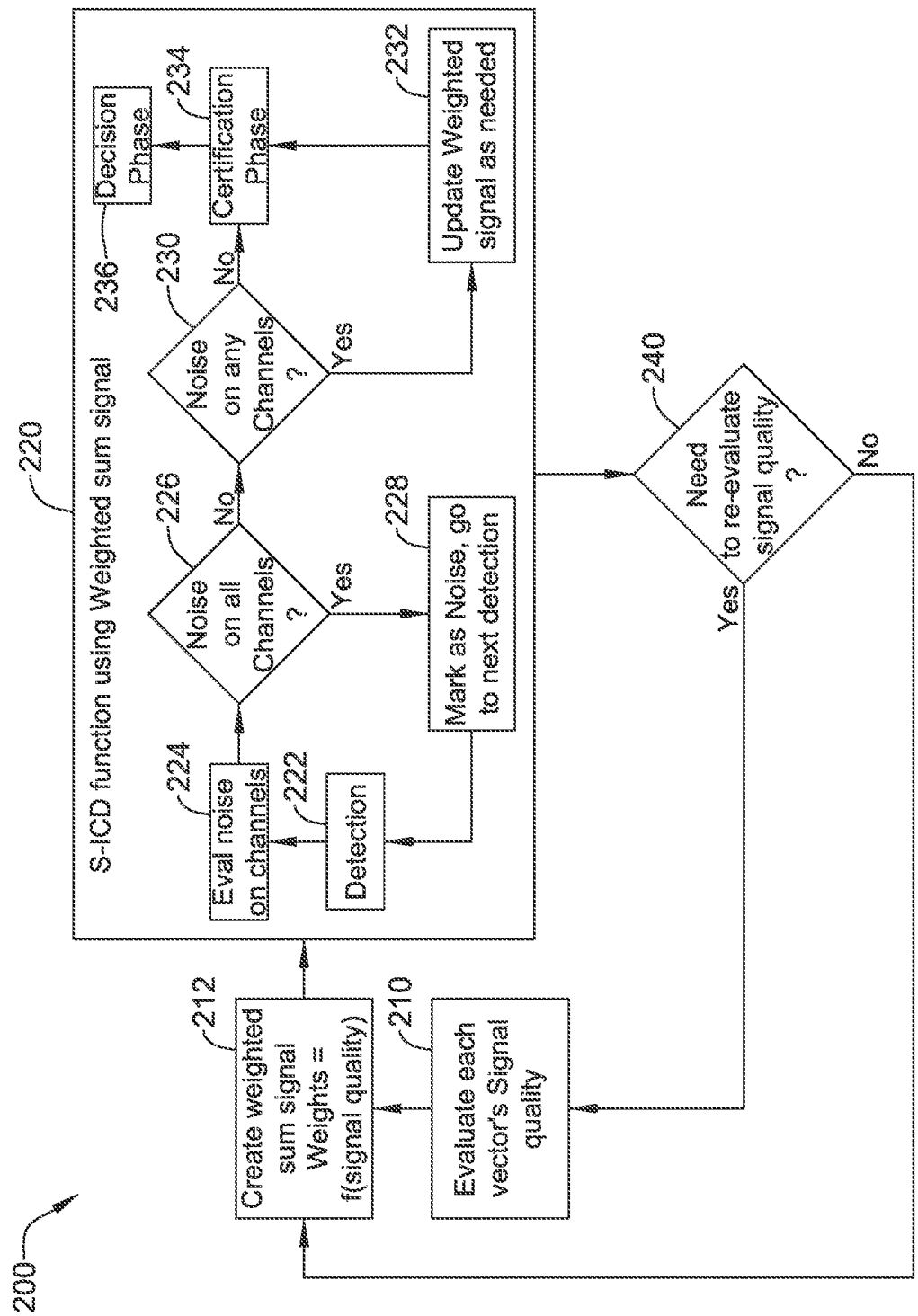

FIG. 3-5 show illustrative methods in block flow form. A first illustration in FIG. 3 shows the combination of multiple vector sensing signals from the very start of analysis. The illustrative method 100 begins by combining signals, as indicated at 110, to convert three data streams S1, S2, S3, indicated at 112, into a combined data stream Sc, as shown at 114.

This combined data stream is then filtered at 120, for example to a bandpass in the range of 3 to 40 Hz, or more preferably about 9 to 25 Hz, or other ranges as suited for a particular application. Filtering 120 may be performed in association with amplification and may be performed on either an analog signal or a digital signal, or both. Filtering may further include DC blocking filters and/or the application of a notch filter(s) to take out 50 and/or 60 Hz line noise.

Weighting factors may be applied to the analog domain signal for example by using adjustable gain circuitry in the input prior to analog-to-digital conversion. Weighting factors may be applied during analog-to-digital conversion, or on the digital signal after analog-to-digital conversion.

The filtered combined signal goes to a detection stage at 122, where individual cardiac cycles or beats may be detected. For example, an amplitude or magnitude measure generated using the combined signal can be compared to a detection threshold, wherein the detection threshold may be a time varying threshold. Upon crossing of the detection threshold, a new cardiac cycle may be declared. Individual detected cycles, standing alone or in small groups, or as a series of events, may then go through a certification stage 124. Certification 124 may include, for example, analyzing one or more signals to determine whether there is noise in the signal, or analyzing detected events in pairs or small groups or as a series to determine whether any overdetected events have taken place. An overdetected event may occur if/when multiple cardiac cycles are declared but only one such cycle took place, or if a cardiac cycle is declared without a new cardiac cycle having occurred. Upon removal of noise and overdetections, the certified cardiac cycles are passed to a decision phase 126 which may use one or more of the rate at which cardiac cycles are detected and/or the morphology (shape) of the cardiac signals associated with cardiac cycles to determine whether a treatable or otherwise targeted cardiac state is occurring. The decision phase 126 may include updates to the heart rate 128.

Returning now to block 110, there are several enhancements available in several different illustrative examples. For example, assuming three sensing vectors (though more or fewer can be used), the combined data stream Sc can be calculated as using this formula:

$$S_c = k_1 * S_1 + k_2 * S_2 + k_3 * S_3 \quad \text{(Formula 1)}$$

In this equation, each of the k-factors is a weighting factor. The weighting factor may be determined by consideration of one or more signal quality metrics. For example the weighting factor for the nth sensing vector may be generated as:

$$k_n = A_n * R_n * V_n * M_n * P_n * N_n$$

Where A is an amplitude measure for the desirable signal of the nth vector, such as the peak cardiac R-wave, the largest excursion from baseline during a QRS complex, or the peak-to-peak measurement of the QRS complex. A larger amplitude measure, within boundaries for the dynamic range of the device hardware, generally would yield a higher value for A. As an alternative, the factor A may be used to correct for amplitude variation for high quality vectors; for example, in the above math, the fact that one sensing vector signal has higher amplitude would already weight that signal higher than a lower amplitude signal without separate application of a weighting factor; therefor the A factor may be used to normalize amplitude for any sensing vector signal that is in a desired range above the noise floor and below the maximum dynamic range for a device. An alternative formulation may take the form of:

$$k_n = f(A_n, R_n, V_n, M_n, P_n, N_n)$$

Where the weighting factor, k, may be a function or set of functions of the various component using, for example, exponential or logarithmic values and/or look-up tables, or addition, subtraction and other operators.

The individual factors may vary widely. The factor R may be a ratio of the desirable signal to a noise measure, for example, the ratio of the R-wave to the next highest peak, T-wave, or average signal amplitude or magnitude of the nth vector. A higher ratio of signal to noise may yield a higher value for R. V may be a measure of variability and/or stability for a given vector, where variability may be determined in any of several ways. For example:

the QRS width may be calculated for each of several cardiac cycles, and variability of the width may be used;

R-wave peak height may be calculated and its variability determined;

Signals for several cardiac cycles may be laid atop one another and cross correlation, sample by sample variation, or other measures of cycle to cycle variation may be determined;

Lower variability may be used to make for a larger value for V. M may be a shape matching score, where shape matching indicates that the detected cardiac cycles correlate to a stored template; a higher match may yield a higher value for M.

P may serve as a correction factor to accommodate the polarity of the signal in a given vector, where P is positive unity (+1) if the signal polarity is positive, or negative unity (−1) if the signal polarity is negative. For example, if cardiac R-waves are the desired signal and focus for later detection steps, P would be used to ensure that the summation to generate the combined signal does not cancel out the desirable signal where one vector has R-wave peaks that are positive, and another vector has R-wave peaks that are negative. Alternatively, rather than including a polarity factor, the system may instead use magnitudes or absolute values to prevent cancelling out.

P may indicate whether signal polarity suggests poor signal quality. For example, polarity may be identified for individual cardiac cycles by identifying, for example, the largest peak, or the first in time peak of the QRS complex, or the peak having the greatest energy, and associating whichever polarity, positive or negative, the identified peak has as the polarity of the signal for a given cardiac cycle. In some embodiments, polarity may be used to select a fiducial point for template alignment or a template for comparison; variation in polarity can make template analysis unreliable. If identified polarity changes from beat to beat or across a set of detections, this may be used to identify poor signal quality.

A noise factor, N, may be included as well. The noise factor may be determined by, for example, determining the average, mean, or RMS value over a block of time (i.e. one second) for a given sensing vector, or for a portion thereof after excluding a desirable signal such as the cardiac R-wave or P-wave either by subtraction or by windowing out a part of the time interval. Higher average, mean, or RMS values are likely related to noisier vectors. The number of turning points or inflection points in the signal may be counted, as higher numbers of turning points or inflection points can suggest a noisier sensing vector. More noise may equate to lower quality and hence a lower value for N.

A further example may include a factor to account for the likelihood of overdetection occurring on a given vector, either projected by analysis and/or based on history of a given sensing vector; such a factor could be, for example, one minus the percentage of detected beats in a previous day, hour or other period of time, which have been marked as double detection for a given sensing vector. Since the certification stage 124 where overdetection or noise detections are flagged is performed in method 100 on the combined signal (after filtering 120 and detection 122), the method may take advantage of parallel processing capabilities to process a combined signal for purposes of analyzing cardiac rhythm on one data stream or channel, and processing a selected individual sensing vector signal for purposes of updating the weighting factor k for a given vector, including such steps as identifying any of the above subcomponents of the weighting factor as well as applying certification assessments to identify noise or overdetection.

The mathematical functions of addition and/or multiplication may be swapped with each other or with other methods. Fewer, more, or different factors may be provided as components of the weighting vector. In one example, each of the components is scaled to within boundaries of 0 to 1, except for the polarity value P that, as noted, may be +1 or −1 in an example. Scaling need not be applied. If desired, one or more of the vectors can be excluded from analysis by reducing the k-factor to zero for the data stream generated from the excluded vector.

In an example, a physician or other user input may also be used to modify the weighting factors k1, k2, or k3, if, for illustration, the physician determines that one sensing vector is unsuitable for use. In another example, a secondary process such as a lead monitoring function may be used to modify or zero out one of the weighting factors if, for illustration, a lead or electrode is determined to be floating (that is, its position is poorly controlled), damaged, or fractured, for example.

In another example, an attempt at forming a template of an ongoing cardiac rhythm may occur, in which template formation calls for a match of a given cardiac cycle signal to one or plural adjacent cycle signals; failure of template formation would indicate a varying signal and may be used to determine that a given sense vector is of lower signal quality. In several examples, one or more of the weighting factors k1, k2, k3 and/or the components thereof are recalculated in one or some combination of the following:

All or some components are recalculated with each new detected cardiac cycle;

All or some components are recalculated at regular intervals (i.e. time blocks of 1 to 60 seconds, for example, or more or less);

All or some components are recalculated in response to a triggering event, where a triggering event is one or more of:

Determination that a patient has changed postures;
Detection of a change of intrinsic cardiac rate;
Identification of one or more noisy or overdetected cardiac cycles;
Determination that the detected heart rate has exceeded a threshold or fallen below a threshold;
Determination that signal quality of one or more sensing vectors has changed by periodic or continuous review of signal quality for one or more such vectors;
Determination that signal quality represented in the combined signal Sc has changed;
In a device that uses one or more of an X-out-of-Y counter or number of intervals to detect (NID) analysis to determine whether a treatable arrhythmia is taking place, the meeting of a therapy or other threshold by the X-out-of-Y counter or NID analysis;
Divergence between cardiac rate as calculated using the combined signal Sc and a cardiac rate calculated by some other device or method, where, for example, the other device may be a separate cardiac device, a blood pressure sensor, or a pulse oximeter, and/or the other method may be an autocorrelation or other non-cardiac-cycle based measurement of cardiac rate;

Recalculation may also be triggered in response to physician and/or patient input in some examples as provided for example via a patient remote control, an in-home monitoring device for an implantable or wearable device, or a physician/clinical programmer.

Autocorrelation is noted in the above list and may take the form as shown in copending U.S. patent application Ser. Nos. 14/819,817, 14/819,851, and 14/819,889, the disclosures of which are incorporated herein by reference. Autocorrelation may also be performed using other methods.

FIG. 4 shows another example. Here, a filtering step 150 is performed first on a set of signals 152, which are then passed at 154 to a combining step 156. The combined filtered signal 158 (as opposed to the filtered combined signal 114 in FIG. 3) passes to detection 160, certification 162, decision stage 164, and updating the heart rate 166. The difference relative to FIG. 3 is that the signal combination takes place after filtering has been performed.

FIG. 5 shows another example method 200. This example includes an evaluation of sensing vector signal quality at 210, creation of weighted sum signal at 212, analysis of the cardiac signal at 220, and a determination of whether there is a need to re-evaluate signal quality at 240. Step 240 may consider any of the triggers noted above for recalculation of vector weights using vector signal quality. If there is no need to recalculate signal quality at block 240, the method loops to 212 where a new weighted sum signal is calculated.

Within block 220, the method waits for a detection 222 of a new cardiac cycle. Noise is evaluated on each of the sensing vector channels 224, which may encompass all or a subset of the individual sensing vectors. A determination is made at 226 whether there is noise on all of the sensing vector channels 224. If so, the new detection from block 222 is marked as noise as indicated at 228 and the method returns to block 222 to await a next detected cardiac cycle.

If block 226 yields a no result, the method determines at 230 whether there is noise on any channel; if so, the weight applied to one or more signals at step 212 may be adjusted as indicated at 232, including, for example, setting the weight to 0 for sensing vectors that are noisy either one time or persistently. Next, the certification phase is applied at 234 (after either of block 230 or 232) to eliminate overdetection or noise on the combined signal itself. The process then goes to the decision phase 236 and may include updating the calculated heart rate, if desired.

An outcome, or quantity of outcomes, finding noise in one or both of blocks 226 and/or 230 may be used to trigger a decision to re-evaluate signal quality in block 240 in some examples.

In an alternative embodiment, the combined signal may use a vector math approach in place of simple summation shown in Formula 1, above. For example, a plurality of sensing vectors may be combined in the following manner to yield a "conversion" to a spherical set of coordinate values:

$$r = \sqrt{(k_1 * S_1)^2 + (k_2 * S_2)^2 + (k_3 * S_3)^2}$$

$$\theta = \cos^{-1}\left(\frac{k_1 * S_1}{r}\right)$$

$$\varphi = \tan^{-1}\left(\frac{k_2 * S_2}{k_3 * S_3}\right)$$

Figure 6:
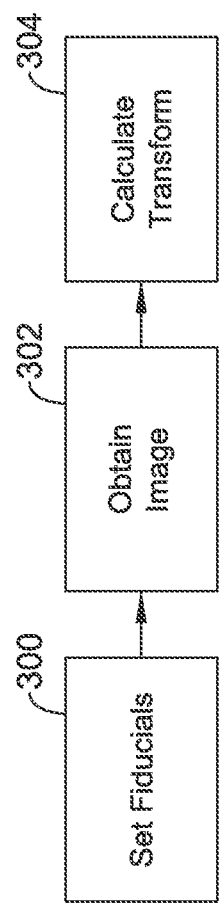

This basic approach presumes that the three sensing vectors are orthogonal, without correction. This simplification may be sufficient in some contexts. However, it may be useful for some embodiments to include correction factors for each of the k weights to account for non-orthogonal configuration of sensing vectors FIG. 6 provides an example for the generation of corrective inputs. For example, fiducial points may be applied to a patient to provide a frame of reference. For example, the patient may be asked to assume a posture (sitting, standing, lying down, etc.), and fiducials may be applied to the patients skin and or provided in one or more implantable positions in the heart, for example, or by use of a fluoroscopic agent to allow imaging of the heart. The application of fiducials at 300 is followed by obtaining an image at 302, for example by X-ray, and calculating a transformation 304 of the actual physical positions of the electrodes of an implant to the position of the heart of a patient. This way, an actual cardiac vectorcardiogram can be generated relative to the positioning of the physical features of the heart. The method may be repeated for a plurality of postures in order to allow specific correction for several patient postures, as the relative position of electrodes and the heart, or the electrodes to one another, may change as the patient changes postures.

In a simpler approach, the fiducials 300 are omitted, and the relative placement of electrodes that define sensing vectors may be obtained. Again the assessment may be used to establish correction for various postures.

The outputs of an assessment as in FIG. 6 may be used to establish new weighting factors for each sensing vector to correct for non-orthogonal disposition of the electrodes relative to one another and/or relative to the patient/cardiac frame of reference. In another example, one or plural matrices are stored to provide correction factors by matrix multiplication as follows:

$$\begin{bmatrix} k_1*S_1 \\ k_2*S_2 \\ k_3*S_3 \end{bmatrix} \begin{bmatrix} a & b & c \\ d & e & f \\ g & h & i \end{bmatrix} = \begin{bmatrix} P_1 \\ P_2 \\ P_3 \end{bmatrix}$$

The correction factor matrix may be selectable based on the patient's posture if desired.

From the combination of these vectors, the radius, r, can be used in detection blocks 122 (FIG. 3, after filtering at 120) or 160 (FIG. 4). The angular components may be used in detection if desired, but may also be used in diagnostic or pathological analysis.

In another example, rather than conversion to spherical coordinates, a conversion to cylindrical coordinates may be performed. Once in a cylindrical coordinate system, the three variables would be ($\rho$, $\varphi$, z). The conversion, much like a conversion to spherical coordinates, can take place with or without correction factors that accommodate position of electrodes relative to one another and/or the patient's heart. In some embodiments, the angular component can be ignored (or reserved for pathology analysis), leaving $\rho$ and z, which may be handled using any of the methods shown herein for handling of a weighted sensing vector signal, for example, by combining the signal components prior to filtering or cardiac cycle detection, and/or by combining results from one or more of cardiac cycle detection, certification, and/or decision stage analyses.

Figure 7:
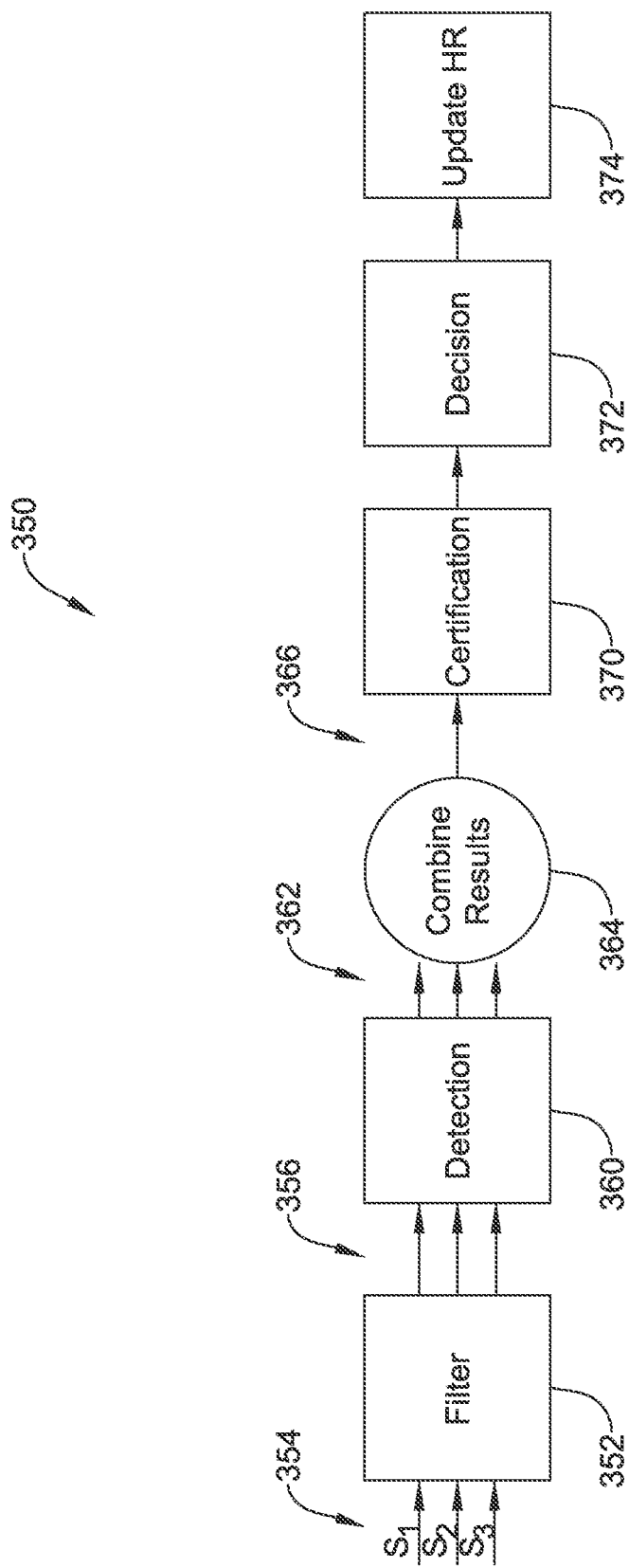
Figure 12:
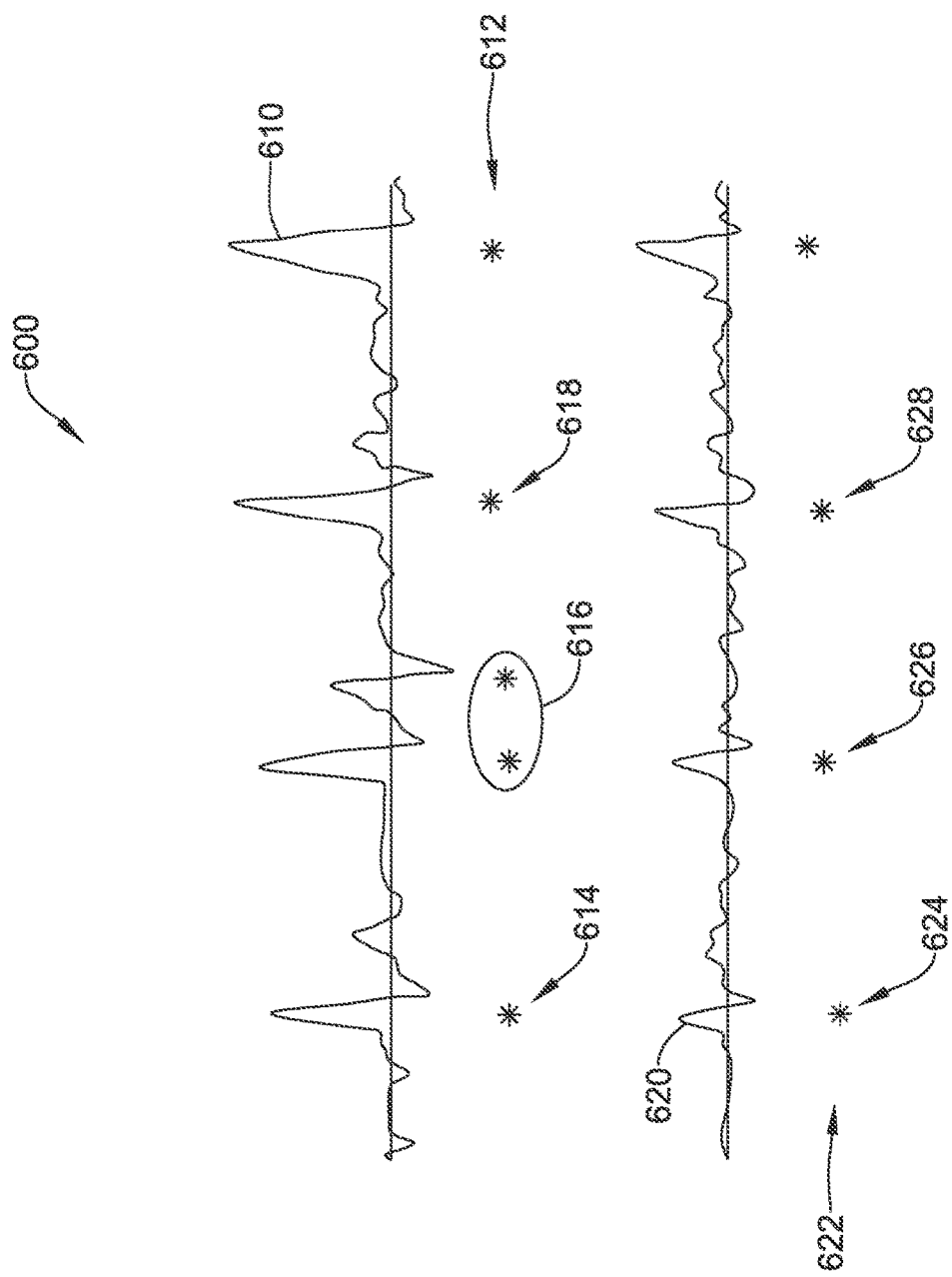
FIG. 12 includes representations of cardiac electrical signals along two sensing vectors and corresponding cardiac cycle detections to demonstrate an illustrative method.
Figure 14:
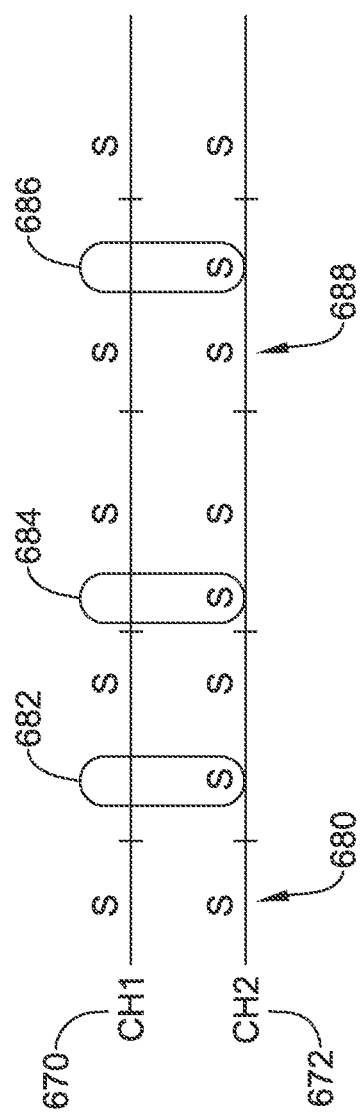

FIG. 7 shows another example in block flow form. In this method 350, filtering 352 occurs on multiple sense vector signals 354. The filtered signals 356 are independently passed to a detection block 360 in which cardiac cycles are detected on each of the incoming signals 356. The output set of detected cardiac cycles on each signal 362 is then combined, as indicated at 364. FIGS. 12 and 14 show pictorial illustrations of how the set of detections can be combined together. In an example, where the cardiac cycle detections match, this can be viewed as likely affirming detection accuracy, and if mismatches occur, this may suggest overdetection, noise, or other difficulty with sensing.

In some examples, spatial differences among the sensing vectors that yield the incoming signals 354 may cause differences in the time at which cardiac cycle detection occurs in each vector. To account for such differences, delays may be integrated where, for example, detection 360 of a cardiac cycle may occur consistently at different times in difference data streams. Such delays may be referred to as phase correction or phase delaying one or more vectors signals and/or data from one or more signals.

Once the cardiac cycle results are combined at 364, the combined data stream 366 is passed on to certification 370 to check for in-signal, as opposed to cross-channel, indications of noise or overdetection. The decision phase 372 and heart rate update 374 follow in this illustration.

Figure 8:
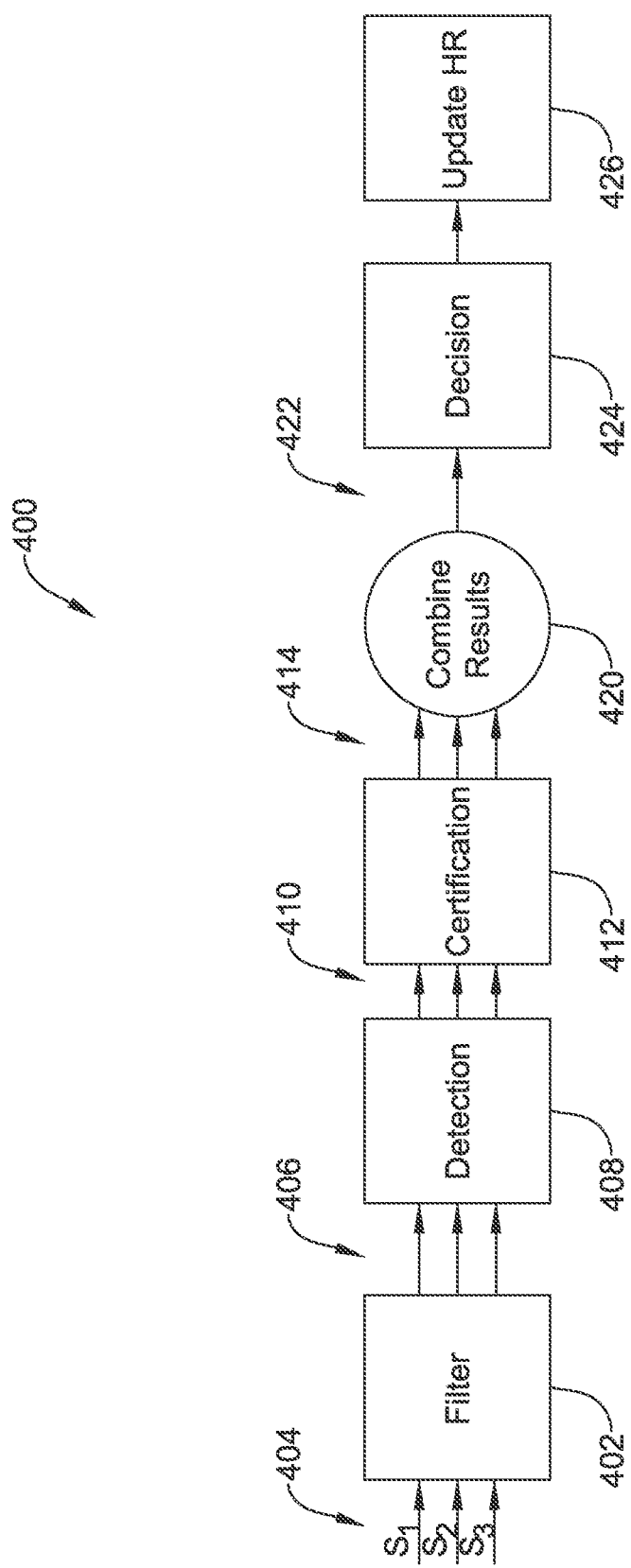

FIG. 8 shows another example in block flow form. In the method 400 filtering 402 is applied to multiple sense vector signals 404. The filtered signals 406 pass to detection 408, yielding data streams of cardiac cycle detections 410. The detections 410 are passed to certification 412 to check for noise or overdetection on the individual channels, with outputs 414 then combined at 420. Examples may be seen in FIGS. 13 and/or 14 of the combining step at 420. In an example, mismatch of detection 408 and/or certification 412 can be used to mark events as suspect, noise, overdetection or true detections, for example. The combined results 422 are passed to the decision phase 424 and heart rate updates 426.

Figure 9:
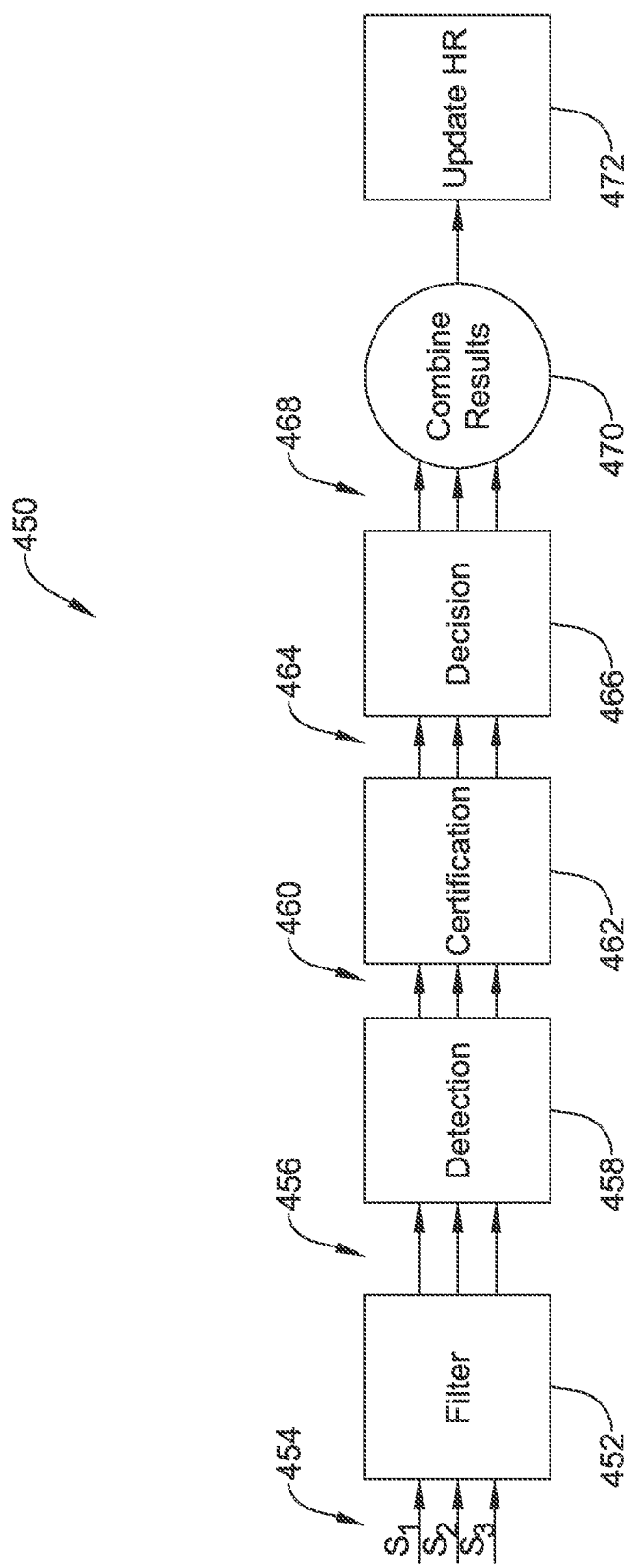

FIG. 9 shows another example in block flow form. In the method 450, filtering 452 is applied to multiple sense vector signals 454. The filtered signals 456 pass to detection 458, yielding data streams of cardiac cycle detections 460 that pass to certification 462 where noise and overdetection can be screened out. Certified cardiac cycle detections 464 pass to the decision phase 466, with decision outcomes 468 then combined at 470, with updates to the heart rate 472. As noted previously, decision phase 466 may assess various elements of the detected signal including the morphology of detected cardiac cycles, rate, variation of the signal from beat to beat, changes relative to a template or multiple templates, width, and overall amplitude to make determinations regarding the cardiac state of the patient.

Figure 10:
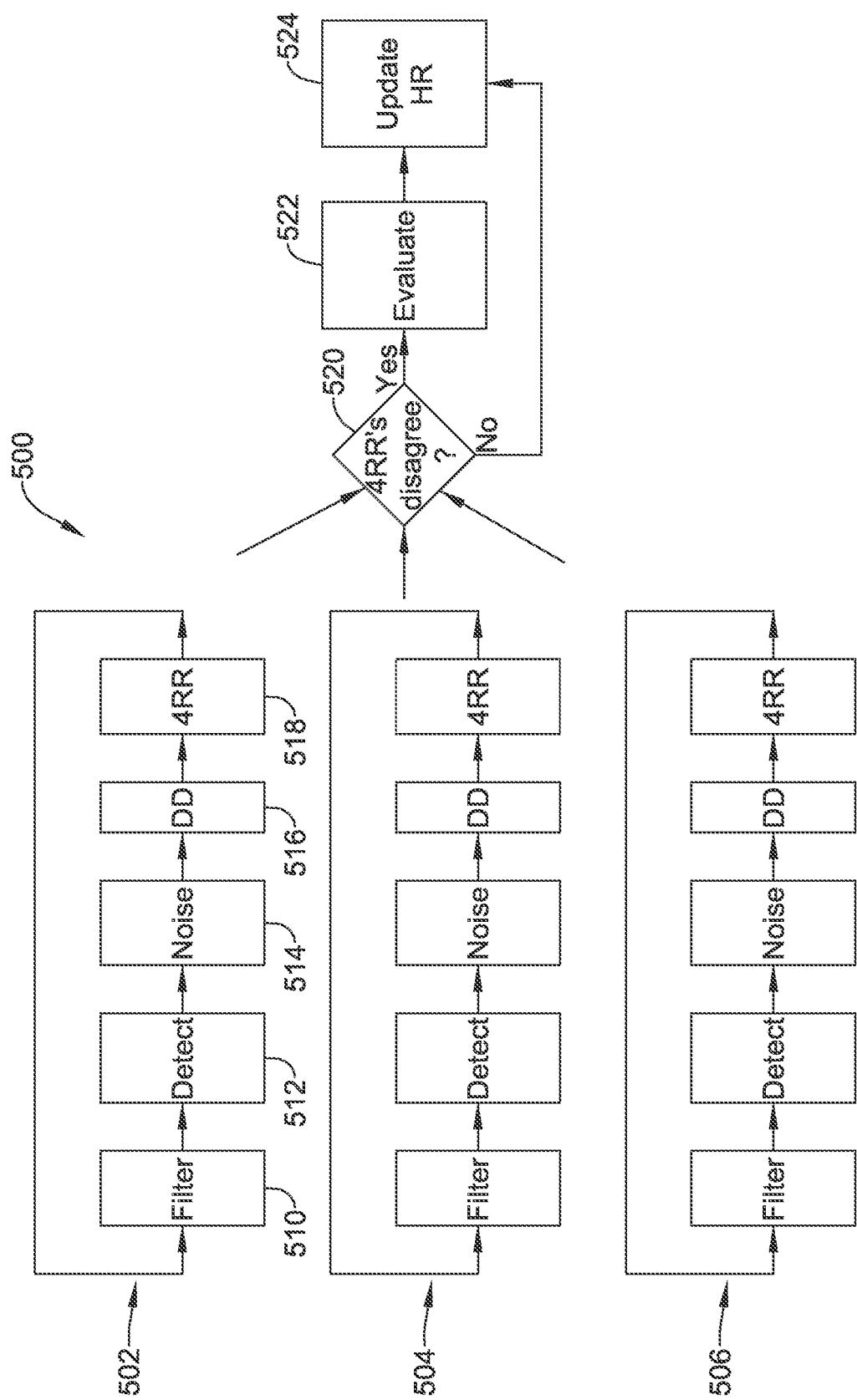

FIG. 10 shows another example in block flow form. FIG. 10 extends the concept of FIG. 9 an additional step. Here there are separate data streams or channels for each of first, second and third sensing vector signals at 502, 504, 506. Each data stream may represent analysis on a single sensing vector, on a combined signal (i.e., k1*s1+k2*s2) as in FIG. 3, or a combined and converted/corrected signal such as the spherical or cylindrical coordinate examples discussed above. In still another example, two or more separate data streams may derive from one source by, for example, subjecting the signal or combination of signals to different weighting factors and/or filtering 510 techniques/boundaries. Each data stream is separately analyzed through filtering 510, cardiac cycle detection 512, noise 514, overdetection 516, and generation of a 4RR (or other average) beat rate 518.

Periodically, or at each detected event detection, or using some other input to drive analysis, a separate assessment is performed in method 500 by comparing the rate results at block 520. If the rate results are in agreement, the overall heart rate can be updated at 524. If the rate results do not agree at 520, then a further evaluation can be performed at 522. Several different techniques may be used at block 522:

In one example, the relative strengths or signal quality for data passed into each of the separate data streams 502, 504, 506 may be compared to one another to determine whether one or more is to be preferred or ignored In another example, a separately sourced heart rate may be referenced using, for example, pulse oximetry, heart sounds, blood pressure measurements, or a rate derived from a second wearable or implantable device, to determine which, if any, of the rates that disagree at block 520 is correct or incorrect.

In another example, a heart rate derived from a non-cardiac-cycle detection methodology, such as the autocorrelation methods referenced above, is obtained to determine which, if any, of the rates that disagree at block 520 is correct or incorrect.

In another example, it may be determined whether mismatch at 520 can be attributed to a chamber-specific cardiac condition, such as a ventricular originating tachyarrhythmia, or a non-conducted, or only partly conducted, atrial flutter or fibrillation.

In another example, simple majority rule is relied upon at 520 if, for example, three data streams are used (as shown), and two of the data streams agree, then the third data stream's calculated rate may be excluded or ignored.

In another example, the detection 512 results from the several data streams can be lined up relative to one another and cross correlated (see FIGS. 12 and 14 below) to determine whether patterns of overdetection may be occurring in more than one data stream, and to see if aligned "true" detections can be extracted to yield a corrected rate.

In yet another example, the mismatch of rate calculations can be used to support a determination of a tachyarrhythmia, if several data streams suggest a tachyarrhythmia, as illustrated for example in FIG. 15, below.

Any of these techniques or combinations thereof may be used to perform evaluation at block 522 to find a heart rate estimate at 524. Other techniques may be used in addition to or instead of the above. For example, in one system, a tiered set of questions is asked:

Do the rates from two of three (or other majority or plurality) channels match; if so, then use the matched rate Do the detections match upon assessment of individual detection streams, either before or after eliminating one or more of noise or overdetection; if so, then use the matched detection data to generate a rate Does one of the sense vectors show a higher sensing quality metric (such as higher amplitude and/or higher signal to noise ratio) than all others; if so, use the rate from that vector These analyses may be used singly or in various combinations.

In another example, within block 522, a set of detections in separate data streams may be assessed for the existence of a pattern or randomness. If mismatch across several vectors occurs randomly, the likely sources are either a noisy signal in one or more sensing vectors or an actual arrhythmia detected on one or more sensing vectors. If, on the other hand, mismatch is patterned, it is likely that malsensing is taking place due to overdetection. For random mismatch, the next step could be to rule out noise (by reviewing, for example, turning point counters for the sensing vectors 502/504/506 and comparing to thresholds or to one another; a vector with far more turning points than the other vectors could be found to be noisy). If noise is ruled out, the fastest rate detected by any of the available sense vectors may be assessed to determine whether a treatable condition is occurring.

Other tiered analyses may be used in other embodiments by combining one or more of the techniques noted for block 522.

Figure 11:
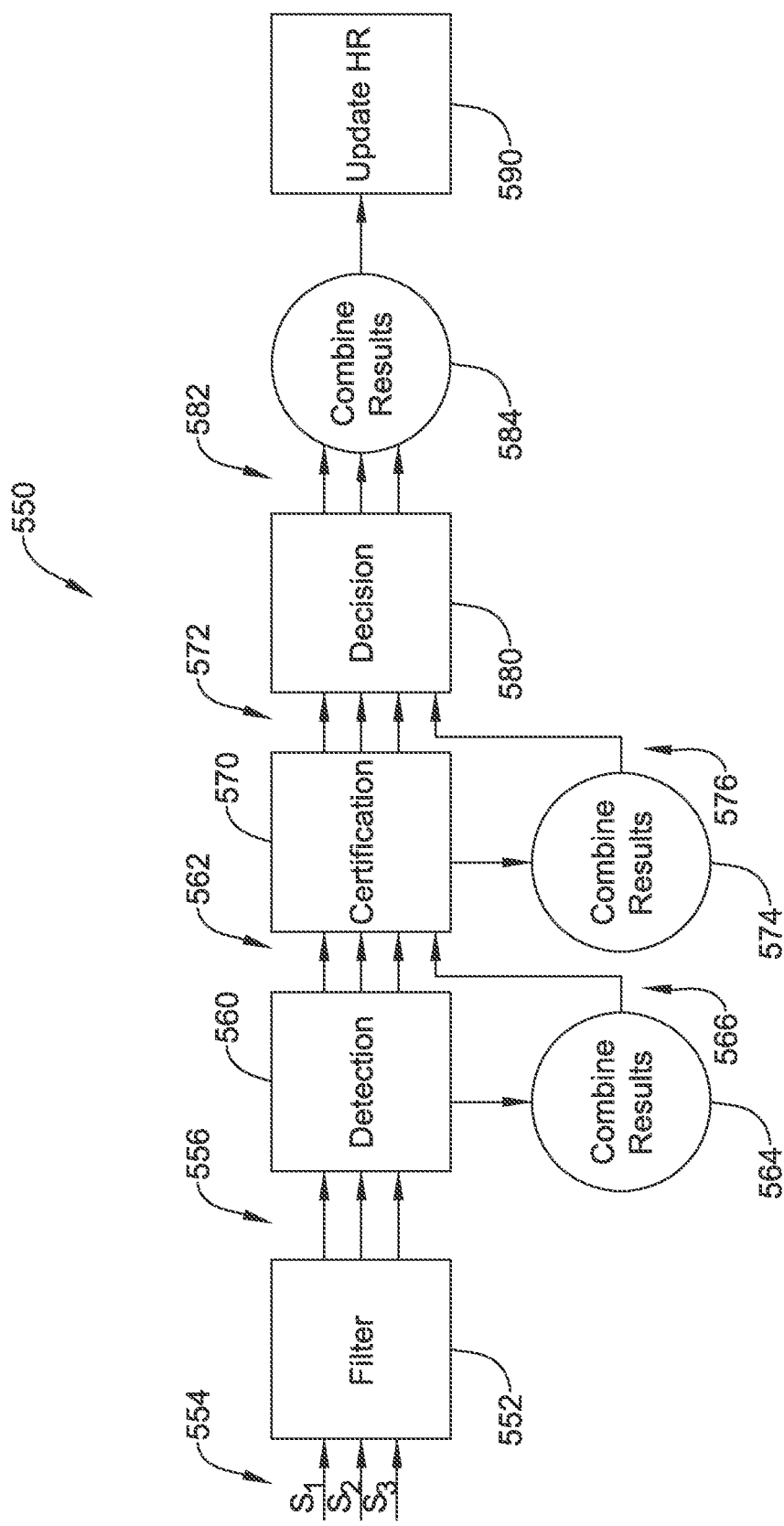

FIG. 11 shows another example in block flow form. Here, results combination occurs repeatedly throughout the process while individual sensing vector analysis continues in parallel. In the illustrative method 550, filtering 552 is applied to multiple sense vector signals 554. The filtered signals 556 pass to detection 560, which provides a set of detection outputs 562. In addition, the outputs of the detection 560 may be combined at 564 in a manner similar to that of block 364 in FIG. 7.

The combined cardiac cycle detection output 566 is passed to certification 570 along with the individual detection outputs 562. Certification 570 again addresses noise and/or double detection to yield output data streams 572 that may include, for example, a data stream for each of the individual detection outputs 562 as well as a data stream for the combined detection results 566. In addition, again, a separate combining block is shown at 574 where the several individual and combination outputs from certification 570 may be combined together in a manner similar to block 420 in FIG. 8.

The now up to five (or more or less) data streams are provided to the decision phase at 580. Here, the method 550 is allowed to consider during the decision phase 580 the individual certified detection outcomes, plus the certified combined detection outcomes, plus the combined certified outcomes. The decision phase 580 may not only assess the cardiac state, but may also identify signal quality metrics by comparing the various results provided to it. The outputs 582 of the decision phase 580 for each individual and combined input can then be combined together at 584 and used to determine not only cardiac state but also to generate an updated rate at 590.

FIG. 12 includes representations of cardiac electrical signals along two sensing vectors and corresponding cardiac cycle detections to demonstrate an illustrative method. The graph 600 shows a first cardiac signal 610 and corresponding cardiac cycle detections 612, and a second cardiac signal 620 with corresponding cardiac cycle detections 622. In this example, the detection outputs 612 and 622 can be compared to one another to identify an overdetection at 616. This is because, while the single detections at 614/624, and later at 618/628 temporally line up with one another, at 616 there are two detections while at 626 there is a single detection. There are several rule sets which can be applied to determine that at least one detection at 616 is an overdetection:

In one example, there must be aligned cardiac cycle detections both before and after the overdetection; here these could be detections 614/624 and 618/628, or, alternatively, one could use the first of the two detections at 616 with detection 626, and subsequent detections 618/628

In one example, there would have to be two closely spaced detections, such as those at 616, with an interval between them of less than a preset threshold or less than approximately half the prevailing interval on either the sensing vector on which an overdetection is found or on a second sensing vector.

In one example a set of two consecutive intervals on one sensing vector/channel have to add up to either a preceding or following interval on that vector. Here, the interval between detections 616, when added to the interval between the latter of detections 616 and detection 618, is the same as the preceding interval between detection 614 and the first of the two detections at 616.

In one example, a set of two consecutive intervals on one sensing vector/channel have to add up to an interval on a second sensing vector. Here, the interval between detections 616, when added to the interval between the latter of detections 616 and detection 618, is the same as the interval from detection 626 to detection 628.

These rules may be used singly or in various combinations. Other rules may apply in addition to or instead of any of these.

Figure 13:
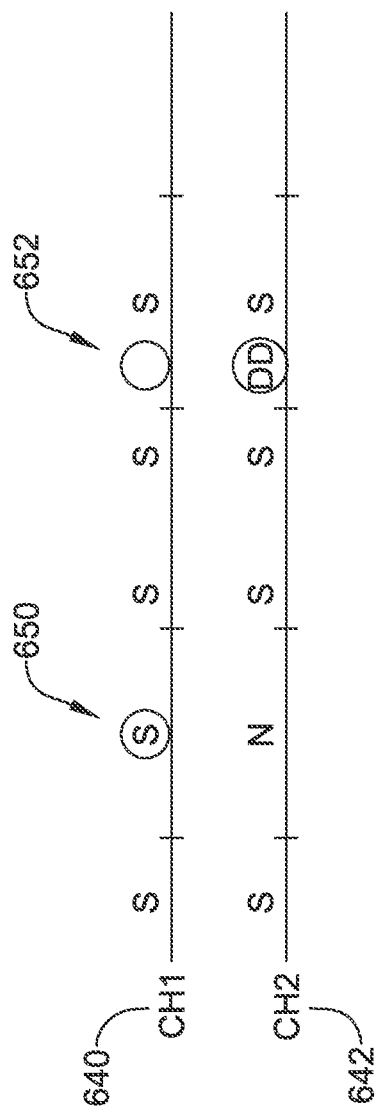
FIGS. 13-15 show cardiac cycle detections in two channels for illustrative methods.
Figure 15:
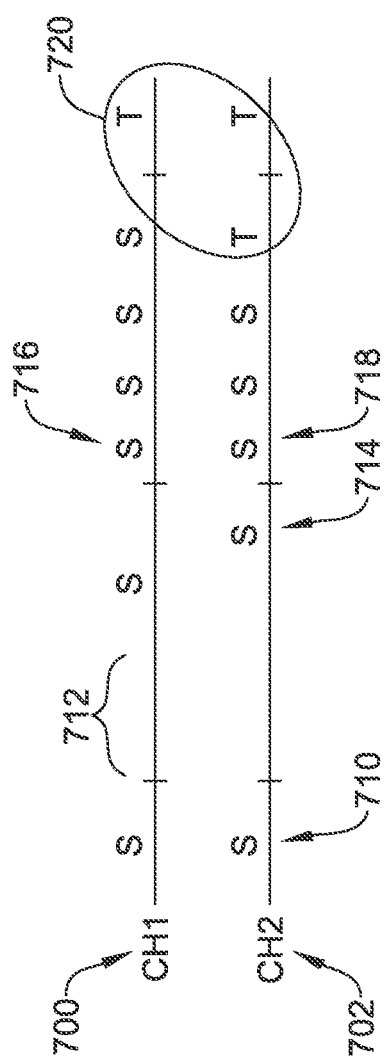

FIGS. 13-15 show cardiac cycle detections in two channels for illustrative methods. FIG. 13 shows cardiac cycle detections, as treated by a certification stage, for a first channel 640 and second channel 642. At 650, a detection takes place in each channel, however, the detection in the second channel 642 is marked as noise (indicated by the "N" marker). This creates a conflict between the two channels 640/642, which can then be resolved in one of several ways:

In one example, the detection at 650 on the first channel is reassessed for noise using a lower standard than previously applied. For example, if a turning points analysis is used for noise in which the number of turning points in a period of time is compared to a threshold and, if the threshold is exceeded, noise is declared, the threshold can be lowered to more readily identify the event at 650 as noise. If the lowered threshold is still passed, the noise flag at 650 may be treated as incorrect; if the lowered threshold is not passed, the noise flag at 650 is confirmed.

In another example, the spectral content of the sensed event at 650 on the first channel 640 is assessed for noise; if the spectral content suggests noise, then noise is confirmed.

In another example, the intervals around the noise flag are analyzed both with and without treating the detection at 650 in each channel as noise. If treating the detection at 650 as noise makes the intervals more consistent, then noise is confirmed; if treating the detection at 650 as not noise makes intervals more consistent, then noise is not confirmed.

In another example, it may be judged whether the two detections at 650 are aligned similar to other detections in each channel; if misaligned, then the noise in one channel may be confirmed while noise in the other channel is not confirmed, suggesting that the noise in one channel may have prevented a true detection from occurring at a different point in time.

In one example, any noise marker on any channel causes treatment of all detections on all channels within a window of time associated with the noise marker as noise.

In another example, when a noise marker is identified, it is next determined whether any of the electrodes used to sense the signal in which the noise marker is placed are being reused by other sensing vectors; if so, the other sensing vectors which reuse one of the electrodes may have any close-in-time detected cardiac cycles also marked as noise.

These rules may be used singly or in various combinations. Other rules may be used in addition to or instead of these.

Also in FIG. 13, at 652, a double detection marker appears in the second channel, but not in the first channel. Here, the double detection marker would be confirmed, as first channel fails to have a corresponding detected cardiac cycle at time 652, but does have 1:1, aligned sensed events around the double detection marker 652. As noted above, other rules may be applied to confirm a certification determination.

FIG. 14 shows another example. Here a string of what may be any of certification outcomes, cardiac cycle detection outcomes, or decision phase outcomes are shown for a first channel 670 and a second channel 672. It can be seen that for the detections on the first channel 670, there are corresponding detections on the second channel on a 1:1 and aligned in time (at least as shown) basis. It should be noted that in some examples, the alignment such as shown at 680 and 688 may be based on the use of an offset applied to data from the first or second channels 670, 672, as detections may occur at consistently offset times in multiple sensing vectors.

For the detections at 682, 684 and 686, which occur only on the second channel 672, the combinational analysis of both sensing vectors reveals overdetection. In one example, a single overdetection event such as at 682 may be identified standing alone. In other examples, multiple potential overdetections in proximity, such as at 682, 684, may be used to confirm suspected overdetection. In still further examples, additional data may be sought to confirm overdetection at 682, 684, 686 by various methods:

In an example, morphology analysis is performed to observe divergence of the detections in the second channel at one or more of 682, 684, 686 from other detections. Divergence may be identified by, for example, looking for differences in overall amplitude, signal width, spectral content, shape (by correlation analysis, principal component analysis, or other review).

In an example, a third data source may be brought to bear, such as a combination of the first and second channels, or review of heart sounds or pulse oximetry data.

The potential overdetections at 682, 684, 686 may be passed through overdetection analysis (such as, for example, in U.S. Pat. Nos. 8,160,686 and 8,160,687, for example) with modified rules that make it easier to identify overdetection such as, for example, if an alternating morphology analysis is used, by using modified thresholds for determining whether a match or no match exists, or by lowering standards used to identify alternating intervals.

These analysis may be used singly or in various combinations. Other analyses may be used in addition to or instead of the above.

FIG. 15 shows an example in which post-decision data streams may be combined (though other steps in the method may be similarly assessed). Here, the combination of data streams confirms a potential arrhythmia pattern. Data is shown for a first channel at 700 and a second channel at 702. At 710, a sensed event or cardiac cycle is observed in aligned fashion on each channel. Following a long pause 712 (which can be a marker of arrhythmia onset), additional sensed events occur at 714, 716, 718 across the two channels, but the sensed events may no longer be aligned (though they could be). Eventually, as shown at 720, the accompanying rate exceeds a threshold such that the "S" markers, which are used in this example for lower rate detected cardiac cycles, become "T" markers indicating a high rate. Misalignment across the two vectors, as well as high rate conditions in each vector, suggest arrhythmia. Moreover, the prior alignment, and long pause 712, are also indicators of tachyarrhythmia. If a noise or double detection marker were to arise in either channel, these factors identified the combination analysis may be used to affirm continued arrhythmia or, alternatively, find a likely sensing problem and potentially delay therapy:

The existence of prior alignment and later misalignment suggests a change in cardiac rhythm, supporting a finding of treatable arrhythmia; conversely consistent and continued alignment may suggest an organized rhythm which may or may not be misdetected.

Figure 16:
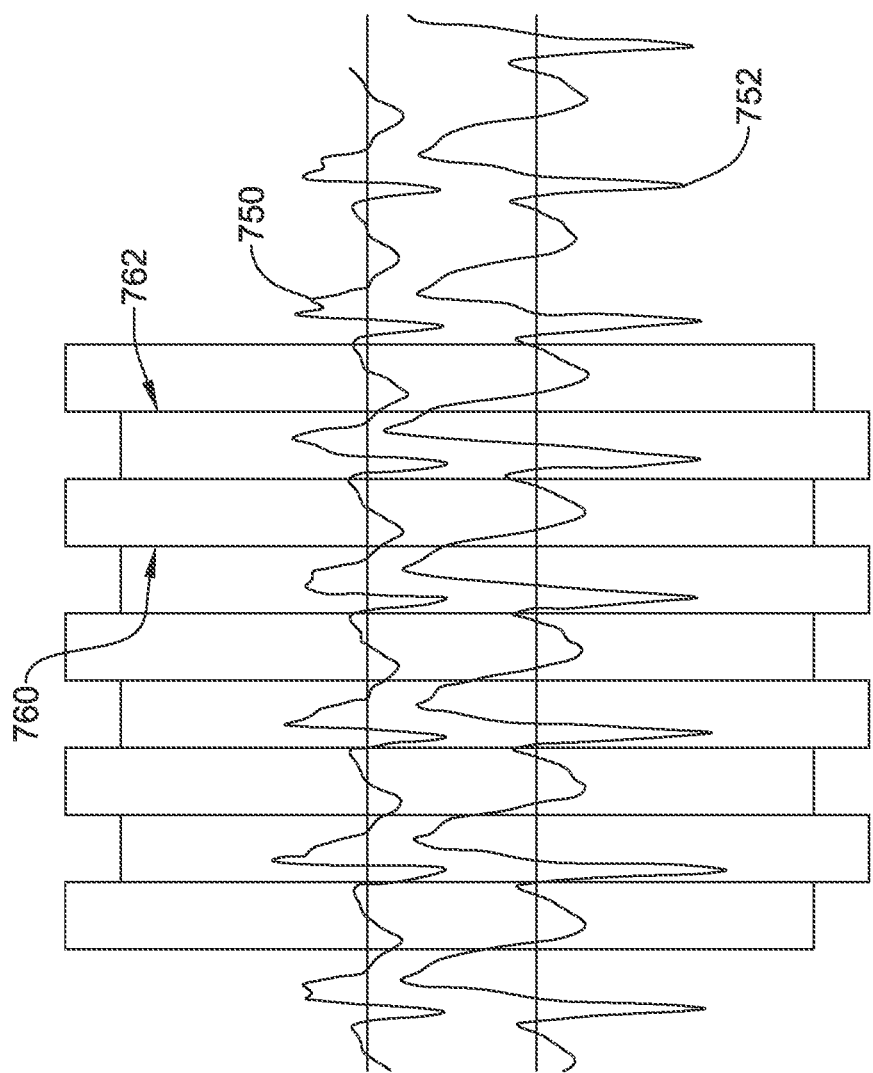
FIG. 16 illustrates a signal analysis method in which a signal is overlaid and summed with a filtered version of itself.

The long pause on each sensing channel followed by the abrupt change in signal characteristic suggests a sudden onset, supporting a finding of treatable arrhythmia; conversely a slower transition to higher rates may suggest an exercise induced tachycardia not needing therapy Lack of noise or double detection markers in each vector suggests arrhythmia detections may be true; presence of one or the other suggests higher scrutiny using additional data input or analysis may be suitable FIG. 16 illustrates a signal analysis method in which a signal is overlaid with a filtered version of itself. For example, a signal from one sensing vector, or a weighted sum of signals from plural sensing vectors, may run through a first data stream or channel subject to a first set of filtering rules, and at the same time, run through a second data stream or channels subject to a second set of filtering rules. The output may be combined, using reference to FIG. 11, after filtering 552 and prior to detection 560, to provide an output for detection purposes.

The example of FIG. 16 goes a step further by switching which operation to perform during different time windows. In this example, the original signal is shown at 750, and the resulting signal is shown at 752. During first window 760, the original signal 750 as filtered with first parameters, is subtracted from itself as filtered using second parameters. During second window 762, the original signal 750 as filtered with the first parameters, is added to itself as filtered using second parameters. The resulting signal emphasizes the signal of the second window 762. The two windows, 760, 762 may be triggered by reference to the original signal 750 as filtered using the first or second parameters, or other parameters, or by reference to some other signal. In one example, the second windows correspond to a time period following cardiac event detection on the signal 750. In this way, signal for use in morphology analysis is generated at 752 by making adjustments in light of the signal 750 used for cardiac cycle detection.

Figure 17:
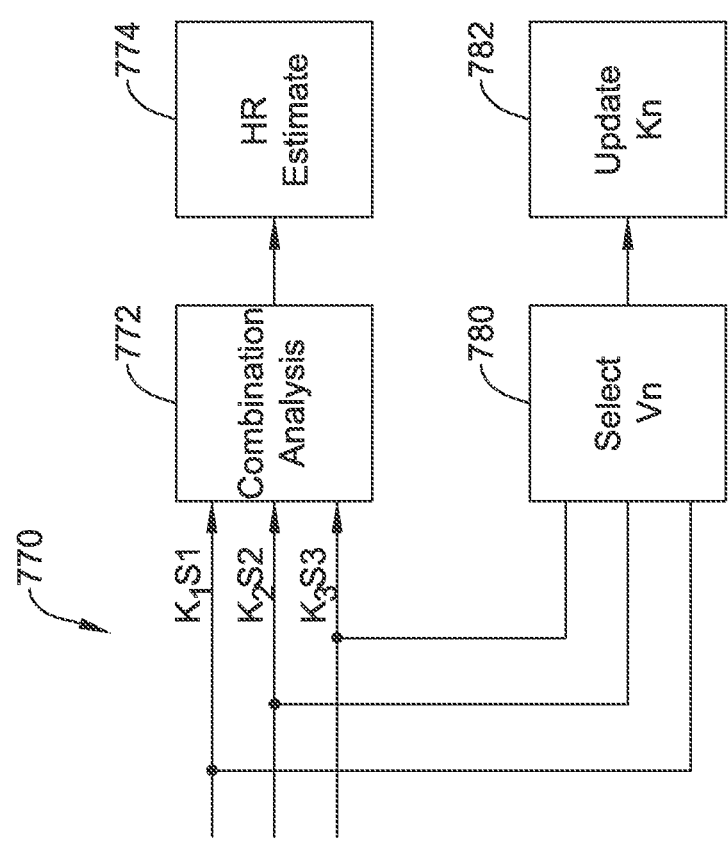
FIGS. 17-20 show illustrative methods in block flow form.

FIG. 17 shows another example in block flow form. In FIG. 17, a plurality of inputs 770 are passed into a combination analysis 772 which may take the forms shown above and/or in FIGS. 18-20, below, leading toward calculation of a new heart rate estimate at 774. The inputs at 770 are each weighted with a corresponding nth weighting factor. In parallel to the combination analysis 772, one of the vectors is selected as shown at 780 and is analyzed at 782 to update the weighting factor for that vector. The selection of a sensing vector at 780 and updating of the weighting factor may be a process that occurs continuously, with different vector selections cycling as completion of updating of a given weighting factor is completed. For example, the updating of weighting factor at 782 may occur each minute for each sensing vector by cycling through each of the vectors in the selection step 780 repeated. Other intervals (every second, minute, hour or once daily) may be used. Rather than, or in addition to, interval based updating, a process of updating in response to a triggering condition may also be used.

Figure 18:
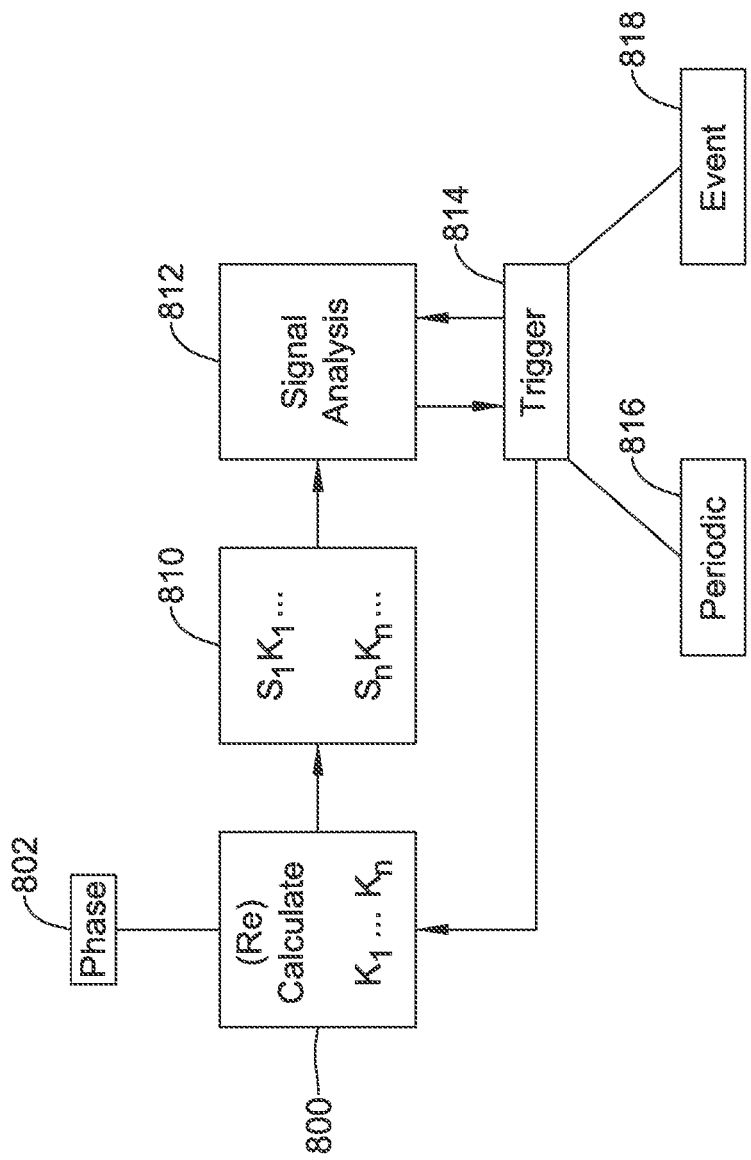

FIG. 18 shows another example in block flow form. Here the method includes calculating a set of weighting factors k1 . . . kn, at 800. Included in this analysis at 800 may be the calculation of phase differences among the vectors, as noted at 802, to allow for alignment of detected cardiac cycles across vectors as in FIGS. 12-15, for example. The calculated weighting factors are used at 810 to modify the sensing data streams, which are subject to signal analysis at 812. A triggering event 814 can be used to exit the signal analysis block to recalculate the weight factors in block 800, again potentially including phase calculation 802. The triggers may be period based 816 (time intervals, for example), or may be based on detected events or conditions 818 such as various occasion-based triggers noted above.

Figure 19:
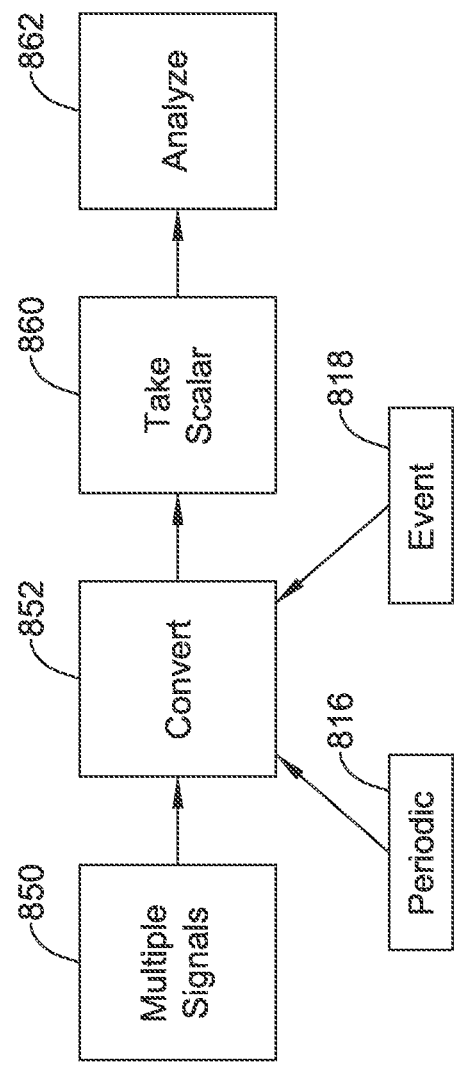

FIG. 19 shows another example in block flow form. In this example, a plurality of signal sources, such as data (weighted or not) from several sensing vectors are captured at 850. These signals are converted at 852 into a separate coordinate system such as cylindrical coordinates to spherical coordinates. In this example, the scalar outputs (that is, omitting the angular outputs of the conversion) are obtained at 860 and pushed to analysis block 862 for cardiac event detection and the like, leading to calculation of a heart rate estimate. If more than three separate vectors are captured at 850, then other conversions may be performed in block 852 to accommodate 4 or more dimensions of the captured signal. Alternatively, the multiple vectors may be cross-correlated or averaged to pare down to a 3-dimensional spatial coordinate for any given sample.

Figure 20:
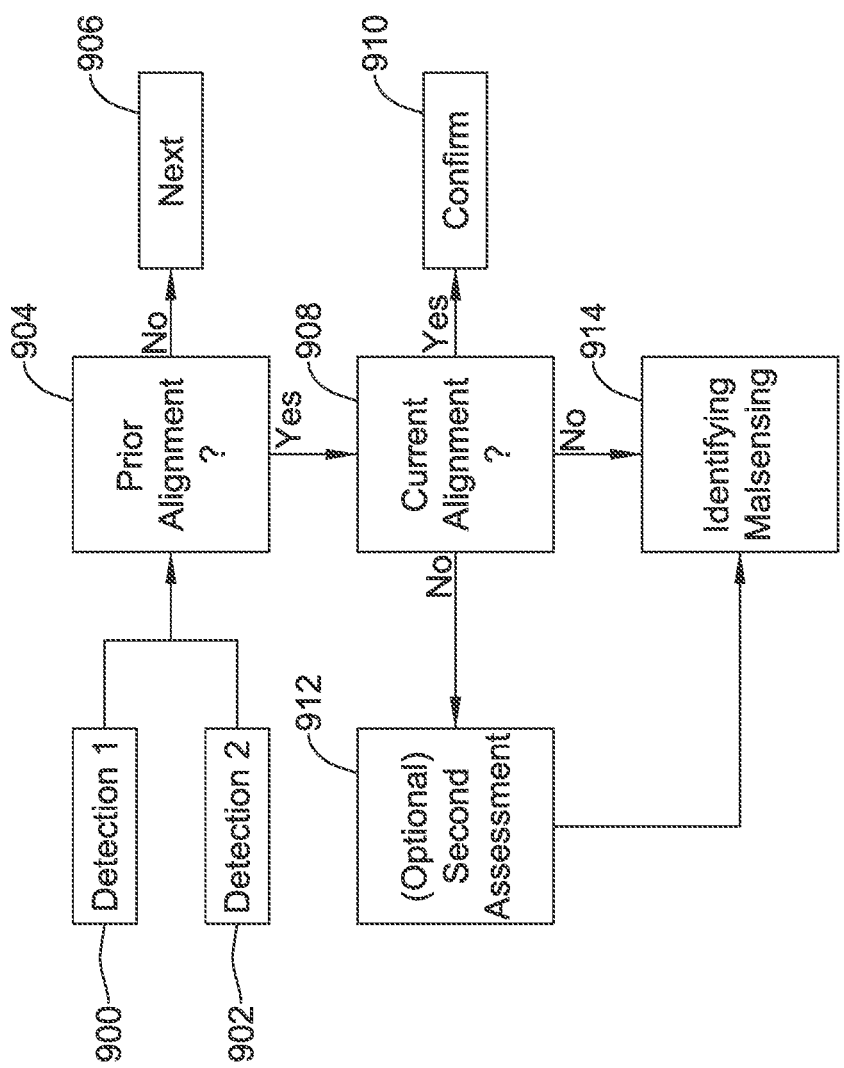

FIG. 20 shows another example in block flow form. Here, first and second cardiac cycle detection data streams are obtained at 900, 902. It is then determined whether for the two streams, prior alignment of data has been observed, as noted at 904. Alignment may refer to the point in time where a detected cardiac cycle is declared, or relative to a fiducial point, such as a highest peak, or inflection point before or after a highest peak. For example, alignment may be found if:

Detections, or fiducial points, in the first stream 900 occur at the same time as detections, or fiducial points, in the second stream 902, or within a predefined window (such as 10-50 milliseconds, or wider or narrower window); or Detections, or fiducial points, in the first stream 900 occur at a stable or predictable delay relative to detections, or fiducial points, in the second stream 902; or Detections, or fiducial points, in the second stream 902 occur at a stable or predictable delay relative to detections, or fiducial points, in the first stream 900.

If there is no alignment, then the method exits at 906, as cross-vector assessment would not yield useful information. A flag may be set at block 906 since one would generally expect that in most systems there would be correlation in time between cardiac cycle detections across vectors. However, with unusual anatomy or cardiac conduction structures/behavior, it is not implausible that a particular system/patient would fail to have the sought-for alignment.

If prior alignment 904 is found, then the method proceeds to determine whether there is a current alignment of cardiac cycle detections at 908. If so, then the detections may be confirmed at 910, subject to assessment for noise and/or overdetection using analysis of the signals in each data stream.

If there is no alignment at 908, this may trigger, optionally, a second assessment as noted at 912. Such second assessments are noted above and may include re-assessment for noise or overdetection of misaligned detected events using modified (reduced) thresholds, for example. Malsensing, if found, may be identified as noted at 914, either after the optional second assessment 912, or automatically from the misalignment found at 908.

The second assessment 912 may confirm the accuracy of detection for extra or misaligned detected events, and would lead to a different outcome than malsensing (not shown in FIG. 20). Such a finding may lead to a conclusion that there has been a change in sensing/detection or cardiac state, or may trigger a secondary analysis to determine whether such a change has taken place; for example, whether any of the current sensing vectors continue to match a template from a known cardiac state may be determined and, if no matches are found, new templates for a new cardiac state may be formed. The method or device may trigger reassessment, for example, of the various sensing vectors available to the system, or the weights or phase delays associated with one or more such vectors, recording of data associated with the potential change of sensing/detection or state, or setting of a flag, for example, to have a physician review captured data.

In another example, malsensing 914 may be identified where previously "aligned" detections across two sense vectors are begin appearing in a different temporal alignment. For example, given vectors V1 and V2, if cardiac cycle detections on V1 and V2 occur synchronously during a first time period, and then later occur with a 60 millisecond offset at a later time, it may be that one of the vectors is no longer triggering cycle detections on the R-wave. For example, the P-wave could be causing cycle detections to occur in one vector, while the R-wave is detected in the other vector; since the P-wave occurs prior to the R-wave, this could lead to an offset. The "Second Assessment" at 912 may include, for example, a peak searching step to determine whether the true amplitude peak for each cardiac cycle in each vector is occurring at an expected time relative to cycle detections, in order to determine which vector is experiencing unexpected detection timing.

The blocks shown in FIGS. 17-20 may each be implemented as means to perform various analysis steps in several ways. For example, a means to calculate a new weighting factor for a given sensing vector may take the form of a block of software code for implementation/execution by a processor, controller, microprocessor or microcontroller. A means to calculate a new weighting factor for a given sensing vector may include or consist of dedicated hardware or an analog, digital or mixed signal application specific integrated circuit (ASIC). Likewise, other blocks on FIGS. 17-20 may be implemented as software and/or hardware.

Figure 21:
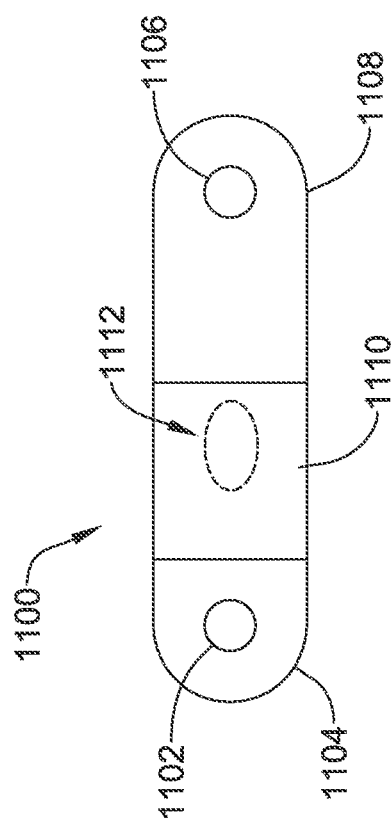
FIG. 21 shows an implantable monitor.

FIG. 21 shows an implantable monitor. An implantable monitor may be implanted subcutaneously in most instances, though other positions such as intracardiac, epicardial, or below the ribs or behind/beneath the sternum may be used instead. The monitor 1100 is shown as having a first sensing electrode 1102 on a header 1104 that may also include, for example, an antenna for communicating with an external or second internal device. A second sensing electrode is shown at 1106 on the opposite end of the device 1100 from the first electrode 1102. The second sensing electrode may be provided on the outside of a battery 1108, for example, which may or may not be rechargeable. Operational circuitry for this design may be provided in the central portion of the device, as indicated at 1110. A third sensing electrode 1112 is shown in phantom to indicate that it may be on the opposite side of the device from the first and second electrodes 1102, 1106. Other dispositions of the multiple electrodes may be used instead, such as those shown in U.S. Pat. No. 5,331,966, or those used in commercially available implantable cardiac monitors such as the various Medtronic Reveal™ products.

Figure 22:
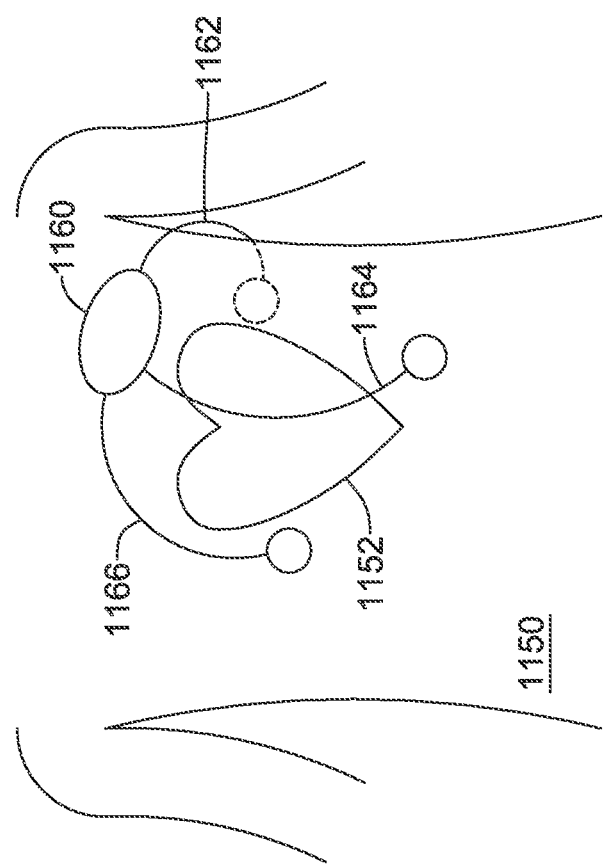
FIG. 22 illustrates a wearable cardiac rhythm management device.

FIG. 22 illustrates a wearable cardiac rhythm management device. The system is shown on the torso 1150 of a patient relative to the heart 1152 of the patient. The external device may include, for example, a canister 1160 having a power source and operational circuitry for the device, as well as a plurality of leads 1162, 1164, 1166 connected to cutaneous electrodes on the front or back of the patient's torso 1150. It is understood that the system may provide therapy or may be merely a monitor, and may take other forms. The system may be, for example, integrated in a wearable vest, or provided as an automated external defibrillator, or may be a smaller wearable product such as a Holter monitor or wearable patch, for example.

For the purposes of the present invention, the implantable therapy system (FIG. 1), implantable monitor (FIG. 21), or external device for therapy or monitoring (FIG. 22) may integrate the various improvements shown herein so long as there are multiple sensing configurations available. While most of the above discussion focuses on the availability of multiple sensing vectors, a sensing reconfiguration may instead call for changing one or more of sensing gain, sensing filtering, data rate, sampling rate, or other sensing features, in addition to or instead of simply considering a different sensing vector.

Various examples above may be implemented in wearable or implantable devices such as the devices shown in FIGS. 1, 21 and 22. Such implementation may take place by including operational circuitry for receiving a signal from implantable electrodes, processing the signal and analyzing the processed signal to make decisions such as whether to store data or deliver therapy. Operational circuitry may be housed in a canister or canisters. The operational circuitry may include a controller (such as a microcontroller or microprocessor, or simply an application specific integrated chip (ASIC) such as an analog, mixed signal, or digital ASIC).

The operational circuitry may instead or also include suitable analog and/or digital circuits needed for signal processing, memory storage and generation of high-power electrical, low-power electrical and/or non-electrical outputs. The operational circuitry may include suitable battery technology for an implantable device (rechargeable or primary cell), with any of numerous examples well known in the art, and may use various capacitor technologies to assist in the short term build-up and/or storage of energy for defibrillation or other output purposes.

The implantable or wearable components may be manufactured with biocompatible materials suitable for implantation or tissue contact, such as those widely known, along with coatings for such materials, throughout the art. For example, implantable devices can be made using titanium, with a titanium nitride or iridium oxide (or other material) coating if desired, and implantable leads can be formed with a biocompatible material such as a polyether, polyester, polyamide, polyurethane, polycarbonate, silicon rubber and blends or copolymers thereof. Alternatively, other biocompatible materials such as silver, gold, titanium, or stainless steel such as MP35N stainless steel alloy, or other materials may be used.

In some examples, the system may include one or more sensors to detect signals in addition to the cardiac electrical signal that can be captured using selected combinations of implantable or wearable electrodes. Such additional sensors may include, for example, temperature sensors, accelerometers, microphones, optical sensors and chemical sensors, among others. The programmer 22 and implantable device 12 may communicate with one another using, for example and without limitation, inductive or RF telemetry, or any other suitable communication solution. The present invention may be embodied in a system having any such characteristics.

A first non-limiting example takes the form of a cardiac rhythm management device having operational circuitry for analyzing cardiac signals using a least first and second cardiac sensing vectors and first and second sensing channels, wherein the operational circuitry is configured to combine the first and second cardiac signals, the operational circuitry comprising the following: a first calculator means for calculating at least first and second weighting factors for the at least first and second sensing vectors (such as circuitry and or programming instructions represented in FIG. 5, block 220, for example); a first means for applying the first weighting factor to modify signals sensed with the first sensing vector (such as circuitry and or programming instructions represented in FIG. 3, block 110, FIG. 4, block 156, or FIG. 5, block 212, for example); a second means for applying the second weighting factor to modify signals sensed with the second sensing vector (such as circuitry and or programming instructions represented in FIG. 3, block 110, FIG. 4, block 156, or FIG. 5, block 212, for example); a first means for combining the signals from the first and second sensing vectors, as modified by the weighting factors, together for analysis to detect cardiac cycles (such as circuitry and or programming instructions represented in FIG. 3, block 110 or FIG. 4, block 156, for example); and recalculation means for causing the calculator means to recalculate the weighting factors on a triggered or continuous basis (such as circuitry and or programming instructions represented in FIG. 5, block 220, for example).

A second non-limiting example takes the form of a cardiac rhythm management device as in the first non-limiting example, wherein the operational circuitry is includes a phase calculator (such as circuitry and or programming instructions represented in FIG. 7, block 360, for example) for calculating a phase factor to apply to delay one of the first or second cardiac signal vectors for the combining step.

A third non-limiting example takes the form of a cardiac rhythm management device as in any of the first two non-limiting examples wherein the operational circuitry includes a third means for applying filtering to the first and second sensing vectors prior to applying the weighting factors (such as circuitry and or programming instructions represented in FIG. 4, block 150, for example).

A fourth non-limiting example takes the form of a cardiac rhythm management device as in any of the first two non-limiting examples wherein the operational circuitry includes a third means for applying filtering to the first and second signals as modified by the weighting factors (such as circuitry and or programming instructions represented in FIG. 3, block 120, for example).

A fifth non-limiting example takes the form of a cardiac rhythm management device as in any of the first three non-limiting examples further comprising: a second means for combining the signals from the first and second sensing vectors together, as multiplied by the weighting factors to yield a combined signal (such as circuitry and or programming instructions represented in FIG. 3, block 110 or FIG. 4, block 156, for example); and sampler means for sampling the combined signal for use in cardiac cycle detection (such as circuitry and or programming instructions represented in FIG. 5, block 240, for example).

A sixth non-limiting example takes the form of a cardiac rhythm management device as in any of the first five non-limiting examples wherein the operational circuitry includes means for performing parallel processing of at least first and second sampled and conditioned data streams, wherein the first data stream comes from one of the at least first and second sensing vectors, as modified by the weighting factors, and the second data stream comes from a combined signal of the first and second sensing vectors (such as circuitry and or programming instructions represented in FIG. 3, block 124, for example).

A seventh non-limiting example takes the form of a cardiac rhythm management device as in the sixth non-limiting example wherein operational circuitry includes means for switching the first data stream between the first and second sensing vectors, wherein the operational circuitry further includes a first means for analyzing the first data stream to update one or more of the weighting factors over time (such as circuitry and or programming instructions represented in FIG. 5, blocks 210, 220, for example).

An eighth non-limiting example takes the form of a cardiac rhythm management device as in the seventh non-limiting example wherein the operational circuitry further comprises: means for periodically switching from the first sensing vector to the second sensing vector for analysis in the second data stream at predefined intervals (such as circuitry and or programming instructions represented in FIG. 10, blocks 520, 522, for example); and means for occasionally switching from the first sensing vector to the second sensing vector for analysis in the second data stream in response to a triggering event (such as circuitry and or programming instructions represented in FIG. 10, blocks 520, 522, for example).

A ninth non-limiting example takes the form of a cardiac rhythm management device as in any of the sixth through eighth non-limiting examples wherein the operational circuitry includes a second means for analyzing the first and second data streams for noise and if noise is found in the first data stream but not in the second data stream, means for modifying a corresponding weighting value for whichever of the sense vectors is in the first data stream at the time of the noise to underweight that data stream (such as circuitry and or programming instructions represented in FIG. 5, blocks 224, 226, 230, 232, 234, for example).

A tenth non-limiting example takes the form of a cardiac rhythm management device as in the ninth non-limiting example wherein the operational circuitry is configured such that if noise is found in the second data stream, one or more detected cardiac cycles is discarded (such as circuitry and or programming instructions represented in FIG. 5, blocks 224, 226, 230, 232, 234, for example).

An eleventh non-limiting example takes the form of a cardiac rhythm management device as in any of the first ten non-limiting examples wherein the operational circuitry is configured such that: the weighting factors are comprised of an ordered series of individual weighting multipliers having at least first and second values (such as circuitry and or programming instructions represented in FIG. 5, blocks 224, 226, 230, 232, 234, for example); the step of applying the weighting factors is performed by determining that a new cardiac cycle has been detected, and then beginning with a first of the ordered series of individual weighting multipliers, multiplying the weighting multipliers by individual signal samples from the sensing vector (such as circuitry and or programming instructions represented in FIG. 5, blocks 224, 226, 230, 232, 234, for example); and the weighting factors vary in weight from one another by having those which are applied first in time be of less weight than those applied later in time (such as circuitry and or programming instructions represented in FIG. 5, blocks 224, 226, 230, 232, 234, for example).

A twelfth non-limiting example takes the form of a cardiac rhythm management device having operational circuitry for analyzing cardiac signals including a least first and second cardiac sensing vectors and first and second sensing channels, wherein the operational circuitry is configured to combine the first and second cardiac signals, the operational circuitry comprising the following: converter means for converting data from the at least first and second cardiac sensing vectors into one of spherical and cylindrical coordinates (such as circuitry and or programming instructions represented in FIG. 19, block 852, for example); generator means for generating a scalar output from the at least one of spherical and cylindrical coordinates (such as circuitry and or programming instructions represented in FIG. 19, block 860, for example); means for performing analysis to detect cardiac cycles using the scalar output (such as circuitry and or programming instructions represented in FIG. 19, block 856, for example); and means for retaining one or more components of the special or cylindrical coordinates to use in addition to the scalar output for identifying overdetection resulting in the step of performing analysis to detect cardiac cycles using the scalar output (such as circuitry and or programming instructions represented in FIG. 19, block 860, for example).

A thirteenth non-limiting example takes the form of a cardiac rhythm management device as in the twelfth non-limiting example wherein the operational circuitry includes means for applying a transformation to a set of data received using the at least first and second cardiac sensing vectors, wherein the transformation is generated by obtaining a normalized data transform to a frame of reference for a patient receiving the implantable cardiac rhythm management device (such as circuitry and or programming instructions represented in FIG. 6, block 304, for example).

A fourteenth non-limiting example takes the form of a cardiac rhythm management device as in the twelfth non-limiting example wherein the operational circuitry includes means for acting upon the components of the converted spherical or cylindrical coordinates by applying a first filtering ruleset to a first data stream, and by applying a second filtering ruleset to a second data stream, and combining results of the filtering of each of the first and second data streams (such as circuitry and or programming instructions represented in FIG. 16, blocks 760, 762, for example).

A fifteenth non-limiting example takes the form of a cardiac rhythm management device having a least first and second sensing vectors and operational circuitry for analyzing cardiac signals on at least three data streams as follows: a first data stream for a signal on the first sensing vector; a second data stream for a signal on the second sensing vector; and a third data stream for a signal calculated as a combined signal generated by combining signals from at least the first and second sensing vectors; wherein the operational circuitry comprises the following: identifier means for identifying a potential new cardiac cycle by analysis of at least the third data stream (such as circuitry and or programming instructions represented in FIG. 5, block 222, for example); means for determining whether there is noise on any of the first, second and third data streams (such as circuitry and or programming instructions represented in FIG. 5, block 224, for example) and, if so, do one of the following: if noise is present on all three data streams, discard data associated with the potential new cardiac cycle (such as circuitry and/or programming instructions represented by blocks 226 and 228 in FIG. 5); or if noise is present on less than all three data streams, change the manner in which the first and second data streams are combined together (such as circuitry and/or programming instructions represented by blocks 230 and 232 of FIG. 5).

A sixteenth non-limiting example takes the form of a cardiac rhythm management device as in the fifteenth non-limiting example wherein the operational circuitry includes combiner means for combining the signals from the at least first and second sensing vectors by applying a first weighting factor to the signal from the first sensing vector, and applying a second weighting factor the signals from the second sensing vector (such as circuitry and or programming instructions represented in FIG. 5, block 212, for example); and the operational circuitry includes means for changing the manner in which the first and second data streams are combined together if noise is present on less than all three data streams by modifying one or more of the weighting factors (such as circuitry and or programming instructions represented in FIG. 5, block 232, for example).

A seventeenth non-limiting example takes the form of a cardiac rhythm management device having a least first and second sensing vectors and operational circuitry for analyzing cardiac signals on at least three data streams as follows: a first data stream for a signal on the first sensing vector; a second data stream for a signal on the second sensing vector; and a third data stream for a signal calculated as a combined signal generated by combining the first and second sensing vectors; wherein the operational circuitry comprises following: a first analyzer means for analyzing the first data stream by filtering the data stream, and a first detector for detecting one or more cardiac cycles in the data stream (such as circuitry and or programming instructions represented in FIG. 10, blocks 510, 512, for example); a second analyzer means for analyzing the second data stream by filtering the data stream, and a second detector for detecting one or more cardiac cycles in the data stream (such as circuitry and or programming instructions represented in FIG. 10, blocks 510, 512, for example); a third analyzer means for analyzing the third data stream by filtering the data stream, and a third detector means for detecting one or more cardiac cycles in the data stream (such as circuitry and or programming instructions represented in FIG. 10, blocks 510, 512, for example); and means for comparing the times at which cardiac cycles are detected in each of the first, second, and third data streams to determine whether any detected cardiac cycles are likely incorrectly detected (such as circuitry and or programming instructions represented in FIG. 10, block 520, for example).

An eighteenth non-limiting example takes the form of a cardiac rhythm management device as in the seventeenth non-limiting example wherein the operational circuitry is configured such that, before comparing the times at which the cardiac cycles are detected in each of the first, second, and third data streams, the operational circuitry first analyzes detected cardiac cycles in the first, second, and third data streams, to eliminate noise-induced detected cardiac cycles.

A nineteenth non-limiting example takes the form of a cardiac rhythm management device as in the seventeenth or eighteenth non-limiting examples wherein the operational circuitry is configured such that, before comparing the times at which the cardiac cycles are detected in each of the first, second, and third data streams, the operational circuitry first analyzes detected cardiac cycles in the first, second, and third data streams, to eliminate overdetected cardiac cycles.

A twentieth non-limiting example takes the form of a cardiac rhythm management device having a least first and second sensing vectors and operational circuitry for analyzing cardiac signals on at least three data streams as follows: a first data stream for a signal on the first sensing vector; a second data stream for a signal on the second sensing vector; and a third data stream for a signal calculated as a combined signal generated by combining the first and second sensing vectors; wherein the operational circuitry comprises the following: a first analyzer means for analyzing the first data stream by filtering the data stream, detecting one or more cardiac cycles in the data stream, and certifying the detected cardiac cycles by removing noise and/or overdetection (such as circuitry and or programming instructions represented in FIG. 11, blocks 552, 560, 570, for example); a second analyzer means for analyzing the second data stream by filtering the data stream, detecting one or more cardiac cycles in the data stream, and certifying the detected cardiac cycles by removing noise and/or overdetection (such as circuitry and or programming instructions represented in FIG. 11, blocks 552, 560, 570, for example); and a third analyzer means for analyzing the third data stream by filtering the data stream, detecting one or more cardiac cycles in the data stream, and certifying the detected cardiac cycles by removing noise and/or overdetection (such as circuitry and or programming instructions represented in FIG. 11, blocks 552, 560, 570, for example); and wherein the first analyzer means, second analyzer means, and third analyzer means are configured to operate in parallel; and wherein the operational circuitry further comprises: a first means for comparing detected cardiac cycles in each of the first, second and third data streams prior to the certification steps for each respective data stream, to identify one or more of likely noise or overdetection (such as circuitry and or programming instructions represented in FIG. 11, block 564, for example).

A twenty-first non-limiting example takes the form of a cardiac rhythm management device as in the twentieth non-limiting example, wherein the operational circuitry further comprises a second means for comparing detected cardiac cycles in each of the first, second and third data streams prior to the certification steps for each respective data stream, to identify one or more of likely noise or overdetection (such as circuitry and or programming instructions represented in FIG. 11, block 564, for example).

A twenty-second non-limiting example takes the form of a cardiac rhythm management device having a least first and second sensing vectors and operational circuitry for analyzing cardiac signals on at least three data streams as follows: a first data stream for a signal on the first sensing vector; a second data stream for a signal on the second sensing vector; and a third data stream for a signal calculated as a combined signal generated by combining the first and second sensing vectors; wherein the operational circuitry comprises the following: a first analyzer means for analyzing the first data stream by filtering the data stream, detecting one or more cardiac cycles in the data stream, and certifying the detected cardiac cycles by removing noise and/or overdetection (such as circuitry and or programming instructions represented in FIG. 11, blocks 552, 560, 570, for example); a second analyzer means for analyzing the second data stream by filtering the data stream, detecting one or more cardiac cycles in the data stream, and certifying the detected cardiac cycles by removing noise and/or overdetection (such as circuitry and or programming instructions represented in FIG. 11, blocks 552, 560, 570, for example); and a third analyzer means for analyzing the third data stream by filtering the data stream, detecting one or more cardiac cycles in the data stream, and certifying the detected cardiac cycles by removing noise and/or overdetection (such as circuitry and or programming instructions represented in FIG. 11, blocks 552, 560, 570, for example); and wherein the first analyzer means, second analyzer means, and means analyzer means are configured to operate in parallel; and wherein the operational circuitry further comprises the following: means for comparing detected cardiac cycles in each of the first, second and third data streams after the certification steps for each respective data stream, to identify one or more of likely noise or overdetection (such as circuitry and or programming instructions represented in FIG. 11, block 564, for example).

A twenty-third non-limiting example takes the form of a cardiac rhythm management device having a least a first sensing vector and operational circuitry for analyzing cardiac signals on at least two data streams, the operational circuitry comprising: receiver means for receiving a signal from the first sensing vector; in a first data stream, a first means for applying a first filtering criteria to the signal from the first sensing vector (such as circuitry and or programming instructions represented in FIG. 16, block 760, for example); in a second data stream, a second means for applying a second filtering criteria different from the first filtering criteria (such as circuitry and or programming instructions represented in FIG. 16, block 762, for example); means for combining the first and second data streams together to create a series of combined sample points for the cardiac signal each having an amplitude determined at least partly from each of the first and second data streams; means for performing cardiac cycle detection on the series of combined sample points (wherein the combined data stream is represented by signal 752 in FIG. 16, and operational circuitry for making such a signal are described in association therewith).

A twenty-fourth non-limiting example takes the form of a cardiac rhythm management device as in the twenty-third non-limiting example wherein the operational circuitry includes means for correcting for phase differences between the first and second data stream prior to or as part of combining the first and second data streams together (such as circuitry and/or programming instructions indicated in block 802 of FIG. 18).

A twenty-fifth non-limiting example takes the form of a cardiac rhythm management device as in the twenty-third or twenty-fourth non-limiting examples wherein each of the combined sample points is generated by adding data from the first data stream to data from the second data stream.

A twenty-sixth non-limiting example takes the form of a cardiac rhythm management device as in the twenty-third or twenty-fourth non-limiting examples wherein each of the combined sample points is generated by adding weighted data from the first data stream to weighted data from the second data stream.

A twenty-seventh non-limiting example takes the form of a cardiac rhythm management device as in the twenty-third or twenty-fourth non-limiting examples wherein the combined sample points are combined together by addition during a first time period, and by subtraction during a second time period, of a cardiac cycle.

A twenty-eighth non-limiting example takes the form of a cardiac rhythm management device having a least first and second sensing vectors and operational circuitry for analyzing cardiac signals on at least two data streams as follows: a first data stream for a signal on the first sensing vector (such as to circuitry and/or programming instructions represented at block 900 in FIG. 20); and a second data stream for a signal on the second sensing vector (such as to circuitry and/or programming instructions represented at block 902 in FIG. 20); wherein the operational circuitry comprises the following: a first detector means for detecting first cardiac cycles on the first data stream (such as to circuitry and/or programming instructions represented at block 900 in FIG. 20); a second detector means for detecting second cardiac cycles on the second data stream (such as to circuitry and/or programming instructions represented at block 902 in FIG. 20); means for determining whether an alignment of the first and second cardiac cycles occurs and finding that alignment has taken place (such as circuitry and/or programming instructions represented at block 904 in FIG. 20); means for observing timing of cardiac cycle detections (such as circuitry and/or programming instructions represented at block 908 in FIG. 20) and, if a spurious detection occurs in the first data stream but not the second data stream, declaring the spurious detection to be one of overdetected or noise (such as circuitry and/or programming instructions represented at block 914 in FIG. 20).

A twenty-ninth non-limiting example takes the form of a cardiac rhythm management device as in the twenty-eighth non-limiting example wherein the operational circuitry includes means for finding that alignment takes place by determining an offset between detection of cardiac cycles in the first data stream and detection of cardiac cycles in the second data stream (such as circuitry and/or programming instructions represented at block 908 in FIG. 20).

Each of the first to twenty-ninth non-limiting examples may take the form of an implantable cardiac rhythm management device having therapy delivery capability for delivering therapy in response to detected treatable arrhythmia or other condition.

Each of the first to twenty-ninth non-limiting examples may instead take the form of an implantable cardiac monitoring apparatus.

Each of the first to twenty-ninth non-limiting examples may instead take the form of a wearable apparatus, with or without therapy capability.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A cardiac rhythm management device comprising at least first and second input nodes to define a least a first sensing vector and operational circuitry for analyzing cardiac signals on at least two data streams, the operational circuitry being configured to:
    receive a signal from the first sensing vector;
    in a first data stream, apply a first filtering criteria to the signal from the first sensing vector;
    in a second data stream, apply a second filtering criteria different from the first filtering criteria applied to the signal from the first sensing vector;
    combine the first and second data streams together to create a series of combined sample points for the cardiac signal each having an amplitude determined at least partly from each of the first and second data streams;

detect cardiac events in the series of combined sample points; and calculate a cardiac rate using the detected cardiac events.

2. The device of claim 1 wherein the operational circuitry is configured to correct for phase differences in the first and second data stream prior to or as part of combining the first and second data streams together.

3. The device of claim 1 wherein each of the combined sample points is generated by adding data from the first data stream to data from the second data stream.

4. The device of claim 1 wherein each of the combined sample points is generated by adding weighted data from the first data stream to weighted data from the second data stream.

5. The device of claim 1 wherein the combined sample points are combined together by addition during a first time period, and by subtraction during a second time period, of a cardiac cycle.

6. An implantable cardiac therapy system comprising the cardiac rhythm management device of claim 1 and implantable electrodes for coupling to the first and second electrical input nodes, wherein the cardiac rhythm management device further includes output circuitry configured to deliver therapy in response to identification of a treatable condition, such identification based at least in part on the cardiac rate, by the operational circuitry and an implantable canister containing the operational circuitry and the output circuitry.

7. A wearable cardiac defibrillator comprising the cardiac rhythm management device of claim 1, a plurality of cutaneous electrodes for coupling to the first and second electrical input nodes, and output circuitry configured to deliver therapy in response to identification of a treatable condition, such identification based at least in part on the cardiac rate, by the operational circuitry.

8. An implantable cardiac monitoring device comprising the cardiac rhythm management device of claim 1, a memory, and an implantable canister containing the memory and the operational circuitry, wherein the operational circuity is further configured to:

determine whether to record data from the first and second data streams by analysis of the cardiac rate; and recording the data in the memory in response to determining to record the data.

9. A wearable cardiac monitoring device comprising the cardiac rhythm management device of claim 1, a memory, and one or more cutaneous electrodes coupled to the first and second inputs, wherein the operational circuity is further configured to:

determine whether to record data from the first and second data streams by analysis of the cardiac rate; and record the data in the memory in response to determining to record the data.

10. A method of operation in a cardiac rhythm management device, the device having at least first and second input nodes to define a least a first sensing vector and operational circuitry for analyzing cardiac signals on at least two data streams, the method comprising the operational circuitry doing each of the following:

receiving a signal from the first sensing vector;

in a first data stream, applying a first filtering criteria to the signal from the first sensing vector;

in a second data stream, applying a second filtering criteria different from the first filtering criteria to the signal from the first sensing vector;

combining the first and second data streams together to create a series of combined sample points for the cardiac signal each having an amplitude determined at least partly from each of the first and second data streams;

detecting cardiac cycles using the series of combined sample points; and calculating a cardiac rate using detected cardiac cycles.

11. The method of claim 10 further comprising the operational circuitry correcting for phase differences in the first and second data stream prior to or as part of combining the first and second data streams together.

12. The method of claim 10 wherein each of the combined sample points is generated by adding data from the first data stream to data from the second data stream.

13. The method of claim 10 wherein each of the combined sample points is generated by adding weighted data from the first data stream to weighted data from the second data stream.

14. The method of claim 10 wherein the combined sample points are combined together by addition during a first time period, and by subtraction during a second time period, of a cardiac cycle.

15. The method of claim 10 wherein the cardiac rhythm management device is an implantable cardiac therapy system comprising implantable electrodes for coupling to the first and second electrical input nodes, output circuitry configured to deliver therapy in response to identification of a treatable condition by the operational circuitry, and a canister housing at least the operational circuitry and output circuitry, the method further comprising the operational circuitry identifying the treatable condition using at least the cardiac rate and delivering the therapy using the output circuitry in response to the treatable condition.

16. The method of claim 10 wherein the cardiac rhythm management device is a wearable defibrillator comprising cutaneous electrodes for coupling to the first and second electrical input nodes and the step of receiving a signal from the first sensing vector comprises receiving a signal from the cutaneous electrodes and output circuitry configured to deliver therapy in response to identification of a treatable condition by the operational circuitry, the method further comprising the operational circuitry identifying the treatable condition using the cardiac rate and delivering the therapy via the output circuitry in response to the treatable condition.

17. The method of claim 10 wherein the cardiac rhythm management device is an implantable monitoring device having a memory and an implantable canister containing the operational circuitry and the memory, and the method further includes the operational circuity doing each of the following:

determine whether to record data from the first and second data streams using the cardiac rate; and recording the data in the memory in response to determining to record the data.

18. The method of claim 10 wherein the cardiac rhythm management device is a wearable monitoring device having a memory and the method further includes the operational circuity doing each of the following:

determine whether to record data from the first and second data streams using the detected rate; and recording the data in the memory in response to determining to record the data.

* * * * *